(12) United States Patent
Evans et al.

(10) Patent No.: US 10,302,619 B2
(45) Date of Patent: May 28, 2019

(54) GREASE WEAR RESISTANCE

(71) Applicants: Jonathan C. Evans, Midland, MI (US); Theodore W. Selby, Midland, MI (US); Marta Manning, Midland, MI (US); Derrick D. Hilliker, Midland, MI (US); Michael A. Habitz, Saginaw Township, MI (US)

(72) Inventors: Jonathan C. Evans, Midland, MI (US); Theodore W. Selby, Midland, MI (US); Marta Manning, Midland, MI (US); Derrick D. Hilliker, Midland, MI (US); Michael A. Habitz, Saginaw Township, MI (US)

(73) Assignee: TANNAS COMPANY, Midland, MI (US)

( * ) Notice: Subject to any disclaimer, the term of this patent is extended or adjusted under 35 U.S.C. 154(b) by 116 days.

(21) Appl. No.: 15/731,024

(22) Filed: Apr. 7, 2017

(65) Prior Publication Data

US 2018/0003692 A1  Jan. 4, 2018

Related U.S. Application Data

(60) Provisional application No. 62/390,773, filed on Apr. 8, 2016.

(51) Int. Cl.
*G01N 33/28* (2006.01)
*C10M 117/02* (2006.01)
(Continued)

(52) U.S. Cl.
CPC ....... *G01N 33/2888* (2013.01); *C10M 105/00* (2013.01); *C10M 105/32* (2013.01);
(Continued)

(58) Field of Classification Search
CPC .............. G01N 33/2888; G01N 33/30; G01N 2291/0226
See application file for complete search history.

(56) References Cited

U.S. PATENT DOCUMENTS 3,998,445 A * 12/1976 Goltz .................... B23Q 3/066
269/258
4,445,365 A    5/1984 Selby
(Continued)

OTHER PUBLICATIONS

Evans et al., U.S. Appl. No. 62/390,773, filed Apr. 8, 2016 A.D., "Grease Wear Resistance."
(Continued)

*Primary Examiner* — Daniel S Larkin
*Assistant Examiner* — Anthony W Megna Fuentes
(74) *Attorney, Agent, or Firm* — Christopher John Rudy

(57) ABSTRACT

Grease wear test device includes a body in a form of a collar having an outer surface, a first side and an opposing second side, which are open to form a hollow, open channel through the body, which has a center axis, into which opposing vee blocks can be inserted; and perpendicular to the center axis, a pair of opposing holes through and open to the outer surface of the body and the cylindrical inside wall, through which a cylindrical test journal (falex pin) can be inserted for contact in general with opposing vee-shaped channels of the inserted, opposing vee blocks, and for rotation during testing. The device can be used to modify a falex pin and vee block device, to receive and contain a small sample of grease or another organic paste product for testing such as a modified version of an ASTM D2670 test method for measuring wear properties of fluid lubricants (falex pin and vee block method).

24 Claims, 23 Drawing Sheets

(51) Int. Cl.
*C10M 121/04* (2006.01)
*C10M 113/06* (2006.01)
*C10M 105/32* (2006.01)
*C10M 105/00* (2006.01)

(52) U.S. Cl.
CPC ......... *C10M 113/06* (2013.01); *C10M 117/02* (2013.01); *C10M 121/04* (2013.01); C10M 2201/056 (2013.01); C10M 2203/003 (2013.01); C10M 2203/10 (2013.01); C10M 2207/2805 (2013.01); C10M 2227/09 (2013.01); C10N 2230/06 (2013.01); C10N 2250/10 (2013.01)

(56) References Cited

U.S. PATENT DOCUMENTS

| | | | | |
|---|---|---|---|---|
| 4,445,678 | A * | 5/1984 | George | B23Q 3/104 |
| | | | | 269/282 |
| 5,388,442 | A * | 2/1995 | Kumar | G01N 19/02 |
| | | | | 73/10 |
| 5,565,621 | A | 10/1996 | Selby et al. | |
| 5,955,655 | A * | 9/1999 | Evans | G01N 33/30 |
| | | | | 73/7 |
| 7,426,855 | B2 * | 9/2008 | Aubele | G01N 3/56 |
| | | | | 73/10 |
| 2005/0092072 | A1 * | 5/2005 | Wollenberg | G01N 3/56 |
| | | | | 73/53.05 |
| 2005/0095718 | A1 * | 5/2005 | Wollenberg | B01J 19/0046 |
| | | | | 436/60 |
| 2013/0333790 | A1 * | 12/2013 | Pinel | C08G 18/10 |
| | | | | 138/145 |
| 2014/0238661 | A1 * | 8/2014 | Gard | E21B 17/042 |
| | | | | 166/242.1 |
| 2016/0272918 | A1 * | 9/2016 | Roberts | C10M 161/00 |

OTHER PUBLICATIONS

ASTM International. ASTM D2670-95 (Reapproved 2010), May 2010.
Panchal et al., *Ind. Crops Prod.*, vol. 63, pp. 48-52, 2015.
Schneider, *J. Sci. Food Agric.*, vol. 86, pp. 1769-1780, 2006.
Kimura et al., *J. Synth. Lubr.*, vol. 20, pp. 241-255, 2003.
Fish, 82nd NLGI Annual Meeting, Coeur d'Alene, Idaho, Jun. 6, 2015.
Kumar et al., *NLGI Spokesman*, vol. 78, No. 5, pp. 24-35, 2014.
Wilkinson et al., *NLGI Spokesman*, vol. 79, No. 2, pp. 6-9, 2015.
ASTM International, ASTM D942-15, Jun. 2015.
ASTM International, ASTM D2266-01 (Reapproved 2015), Jun. 2015.
ASTM International, ASTM D2596-15, Sep. 2015.
ASTM International, ASTM D2509-14, Feb. 2015.
Nagendromma et al., *Lubricants*, 2015, 3, 628-636.
USPTO Patent Full-Text and Image Database, Results of Search in US Patent Collection db for ACLM/about, Hits 1-50 out of 1265342, Feb. 23, 2019 A.D.

* cited by examiner

RATCHET WHEEL LOADER — LOAD GAGE — V-BLOCKS AND JOURNAL — OIL CUP — TORQUE GAGE

RATCHET WHEEL DETAIL

GREASE D, FRESH

GREASE D, OXIDIZED AT 130°C, 100 H, 4 G/PAN

GREASE C, FRESH

GREASE C, OXIDIZED AT 99°C, 100 H, 4 G/PAN

Unpolished

All Parts Polished

Vee Blocks Only Polished

Pin Only Polished Run #1

GREASE WEAR RESISTANCE

This claims 35 USC 119(e) benefit of provisional No. U.S. 62/390,773 filed on Apr. 8, 2016 A.D., the specification of which, to include drawings, is incorporated herein by reference.

FIELD AND PURVIEW OF THE INVENTION

This concerns a device and method for evaluating wear resistance and its effects on grease and other organic paste products. The device and method may be modified from the falex pin and vee block machine and method of the ASTM D2670 fluid lubricant wear property test, now hereby for grease and other organic paste products.

BACKGROUND TO THE INVENTION

Grease-like lubricants from animal fats and the alkaline components of fire-place ash is believed to be the earliest form of man's lubrication for his wooden wheel-and-shaft vehicles. First records noted use in Egypt of such materials blended with lime to lubricate chariots. After thousands of years, as the $19^{th}$ century came to a close, fat- and vegetable-based greases were replaced with more easily manufactured and durable mineral oil based greases. Yet, bio-based greases derived from plant oil feedstock tend to have excellent tribological properties and generally have very high viscosities and flash points. They have some inherent disadvantages, however, such as sensitivity to hydrolysis and oxidation. See, Panchal, T., et al., "Bio-based Grease, a Value Added Product from Renewable Resources," *Ind. Crops Prod.*, 2015, 63, 48-52.

Today's revival of bio-based greases is being driven by an increased global focus towards the use of ecologically-friendly, environmentally safe materials. It is estimated that some 50% of all lubricants worldwide end up in the environment because of total loss applications, volatility, spills or accidents. See, Schneider, M., "Plant-oil Based Lubricants and Hydraulic Fluids," *J Sci. Food Agric.*, 2006, 86: 1769-1780. The introduction of legislation and consumer-driven initiatives such as the U.S. Environmental Protection Agency's Vessel General Permit, the European Union's Ecolabel scheme, and the U.S. Department of Agriculture's BioPreferred program has increased renewable and bio-sourced grease use. Such recent trends have primarily focused the grease industry on price and performance as well as biodegradability and ecological toxicity. See, Kimura, H., et al., "Properties and Applications of Synthetic Greases," *J. Synth. Lubr.*, 2003, 20, 241-255; Fish, G., "The Development of More Environmentally Considerate Greases," $82^{nd}$ NLGI Annual Meeting, Coeur d'Alene, Id., U.S.A., Jun. 6, 2015; Kumar, A., et al., "Challenges in Manufacturing of Bio-Based Greases," *NLGI Spokesman*, 2014, 78(5), 24-35; and Wilkinson, M., et al., "Meeting the Challenges Posed by Environmentally Acceptable Lubricants," *NLGI Spokesman*, 2015, 79(2), 6-9.

On the other hand, the ASTM D2670 method, even as found in its latest iteration, ASTM D2670-95 (Reapproved 2010), "Measuring Wear Properties of Fluid Lubricants (Falex Pin and Vee Block Method)," is limited to testing liquids such as, for example, mineral oils. Moreover, a rather large, 60-mL sample is required to be placed in the sample cup for immersion of the vee blocks during testing.

It would be desirable to improve upon the art of grease evaluation. It would be desirable, moreover, to ameliorate if not overcome drawbacks and shortcomings in the arts and fields such as set forth above. It would be desirable to provide the art of grease evaluation an alternative.

A FULL DISCLOSURE OF THE INVENTION

Provided hereby in address of the foregoing is a method for evaluating wear resistance and its effects on a grease or another organic paste product, which can be a modified version of an ASTM D2670 test method for measuring wear properties of fluid lubricants (falex pin and vee block method), for example, ASTM D2760-95 (Reapproved 2010), comprising providing a modified falex pin and vee block device so as to further include a grease wear test device, the grease wear test device (also termed, "grease sleeve" or "grease holder") including:

a body in a form of a collar having an outer surface, a first side and an opposing second side;

the first and second sides being open so as to form a hollow, open channel through the body having a center axis, into which opposing vee blocks can be inserted; and perpendicular to the center axis, a pair of opposing holes through and open to the outer surface of the body and cylindrical inside wall, through which a cylindrical test journal (falex pin) can be inserted for contact in general with opposing vee-shaped channels of the inserted, opposing vee blocks, and for rotation during testing; and the modified falex pin and vee block device can receive and contain a small sample of grease or another organic paste product such that grease or other organic paste product from the small sample may contact the opposing vee-shaped channels of the inserted, opposing bee blocks, and the cylindrical test journal during the testing, with containment of the small sample provided through employment of the grease wear test device;

the modified falex pin and vee block device is assembled to include the grease wear test device, and the small sample of grease or other organic paste product is provided thereto such that the small sample is received and contained thereby as aforesaid; the modified falex pin and vee block device with the small sample is attached to a falex pin and vee block test machine; and the test machine is actuated with rotation of the falex pin to conduct the testing. Also provided hereby are the grease wear test device, and the modified falex pin and vee block device to include the grease wear test device in both kit form and assembled form.

The invention is useful in testing and evaluation of grease or other organic paste product.

Hereby, the art is advanced in kind.

Thus, ASTM D2760 type testing is brought into a different field, advancing the art of the different field significantly. Thus, the boundaries of ASTM D2670 type testing are dramatically expanded. Whereas this was unheard of before, now grease is subject to ASTM D2670 type testing. Moreover, such testing can be carried out effectively with small samples of the grease. The small sample of grease used in the ASTM D2670 type testing can be of a size such as less than a 4-g sample that is otherwise required in ASTM D942 testing, to include an about 2-g sample or less, an about 1-g sample or less, or an about 0.5-g sample or less. No lubricant cup is required, and desirably is absent, in the present modified ASTM D2670 type testing. Such advantageous practice is provided through the modified falex pin and vee block device, which can be made to include the grease wear test device. Such devices, moreover, are simple in configuration, readily and economically able to be manufactured, easy to employ in testing, and can be adapted as aftermarket retrofit devices for already existing, commercially available ASTM D2670 test equipment. Temperature can be monitored during testing for more data.

The present invention can be employed in conjunction with other test protocols. Thus, for example, such techniques as Fourier transform infra red (FTIR) analysis, and FTIR equipped with attenuated total reflectance (ATR) may be employed to extend application of present methodology. As well, the present methodology may be employed in conjunction with such testing as that of ASTM D942 oxidation testing or modified testing methodology. And so, understanding of a composition from testing can be significantly enhanced.

For example, to examine the impact of oxidation on the anti-wear properties of bio-based and mineral-based commercial greases, a friction and wear test of the oxidized test grease of the present methodology is performed in a special modification of the ASTM D2670 falex pin and vee block test method following oxidation through from modified or unmodified ASTM D942 test methodology. Grease or other organic paste product samples can be employed in an unoxidized state as well, and compared if desired to the samples in an oxidized state, say, from modified or unmodified ASTM D942 test methodology or from samples obtained from employment in the field. The samples may be investigated with other analytical tools as well, for example, sensitive FTIR or ATR-FTIR instrumentation. The present modified approach employs much less sample in testing, particularly as apropos here, than liquid required in standard ASTM D2760 testing, which may accommodate a relatively small volume generated in an associated oxidation test or that which may be available from samples from the field, say, in forensic examinations. The data from these testing protocols can be used together for further, deeper insight into the properties or performance of the grease or other organic paste.

Numerous further advantages attend the invention.

The drawings form part of the specification hereof With respect to the drawings, which are not necessarily drawn to scale, the following is briefly noted:

FIG. 1A is a perspective view of a prior art falex pin and vee block test machine employed as in ASTM D2760 methodology for measuring the wear properties of fluid lubricants, with FIG. 1B being a perspective view of ratchet wheel detail referenced in FIG. 1A by reference numeral 1B. The same compares to a picture taken from the full manufacturer's specification manual on the Falex Corporation website. As shown, in this test method, a sample pan is used to hold a 60-mL liquid test sample in place during testing, FIG. 2 is a view of a grease wear test device, unassembled, as for testing the wear resistance of a grease or another organic paste product.

FIG. 3 is a view of the grease wear test device of FIG. 7, assembled.

FIGS. 4A, 4B and 4C show several views of a grease sleeve/grease holder found within FIGS. 2 and 3, with FIG. 4A being a top view; FIG. 4B being an elevational side view; and FIG. 4C being a perspective view. The grease sleeve/grease holder is in a form of a one-piece collar. Although its material is, for example, #316 stainless steel, another material could be used such as another metal or alloy, a rubber, or a plastic.

Figure 2:
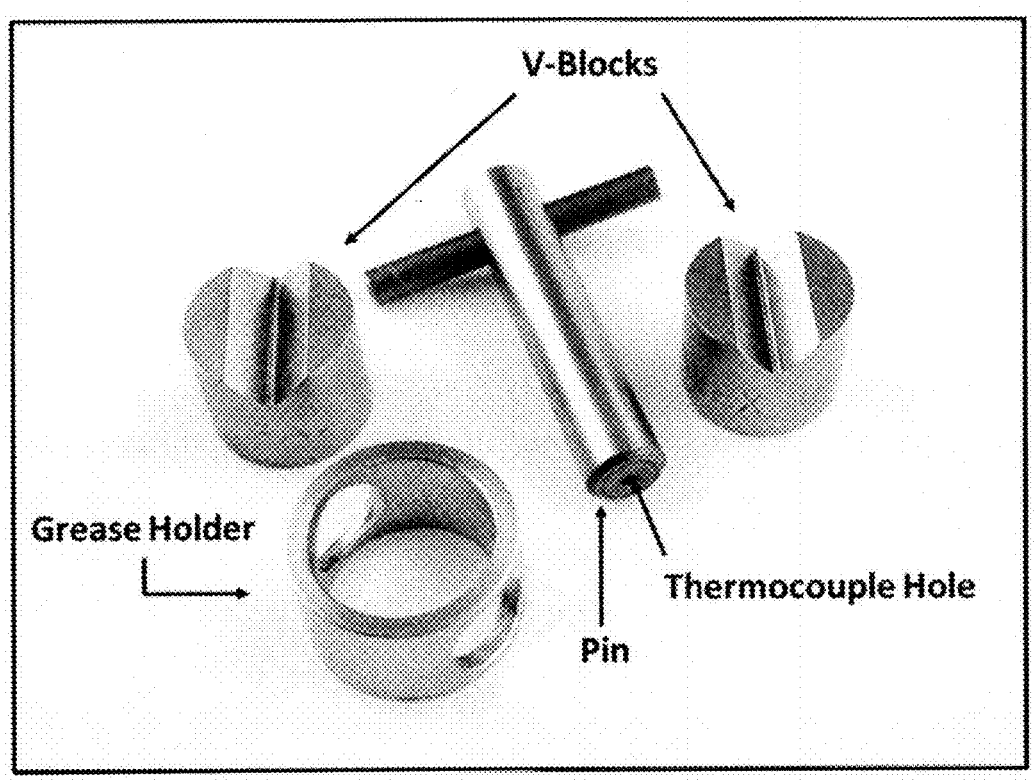
Figure 3:
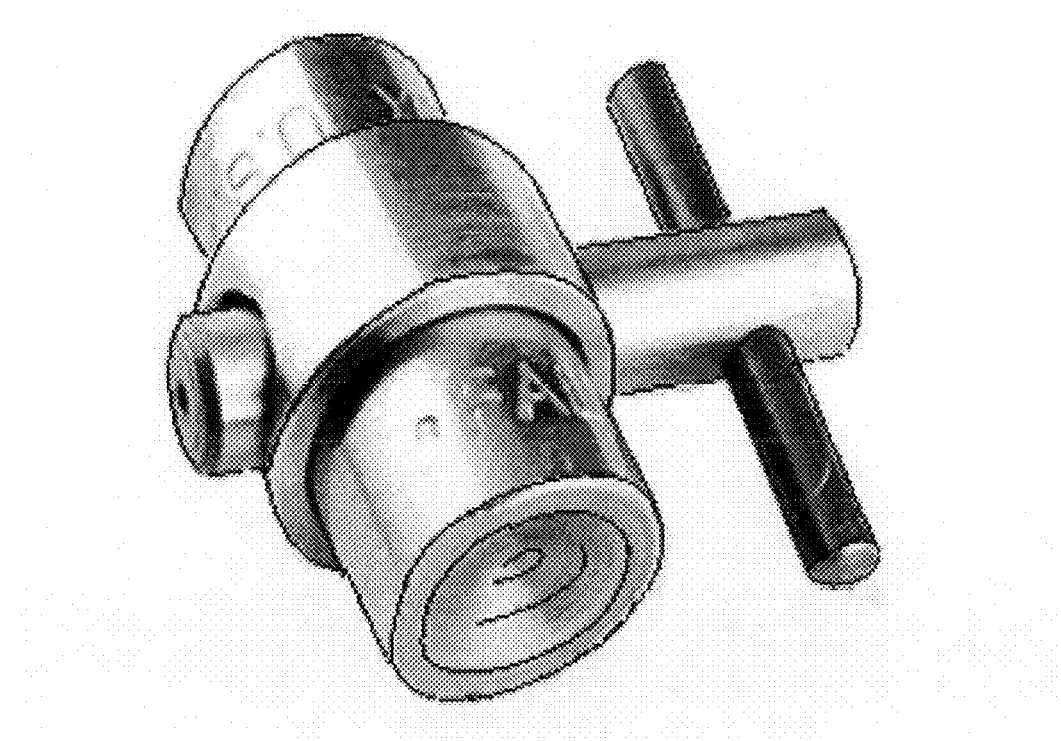
Figure 4A:
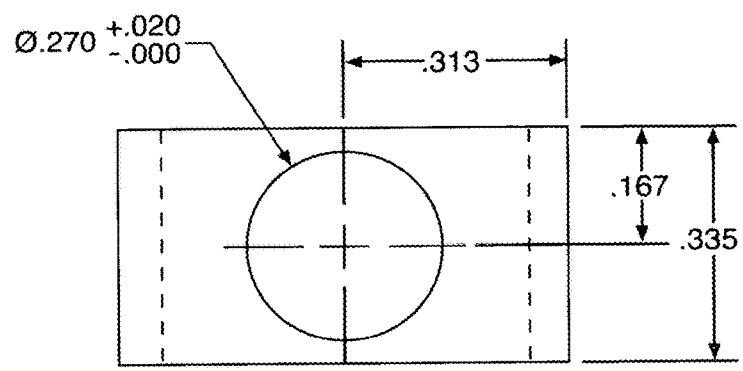
Figure 4B:
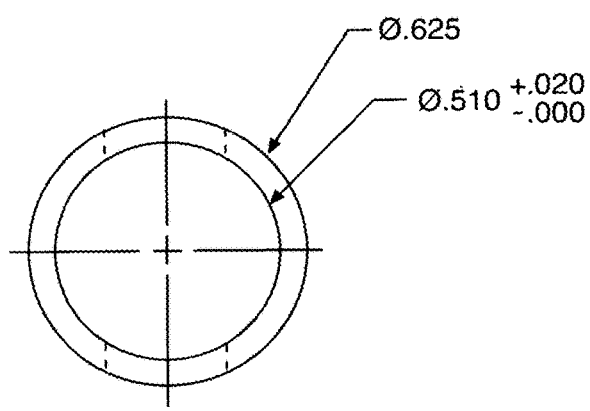
Figure 4C:
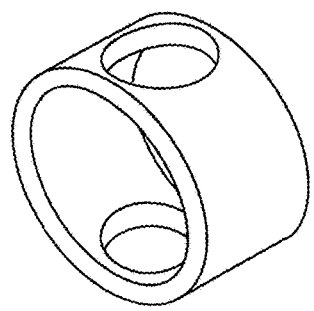
Figure 12A:
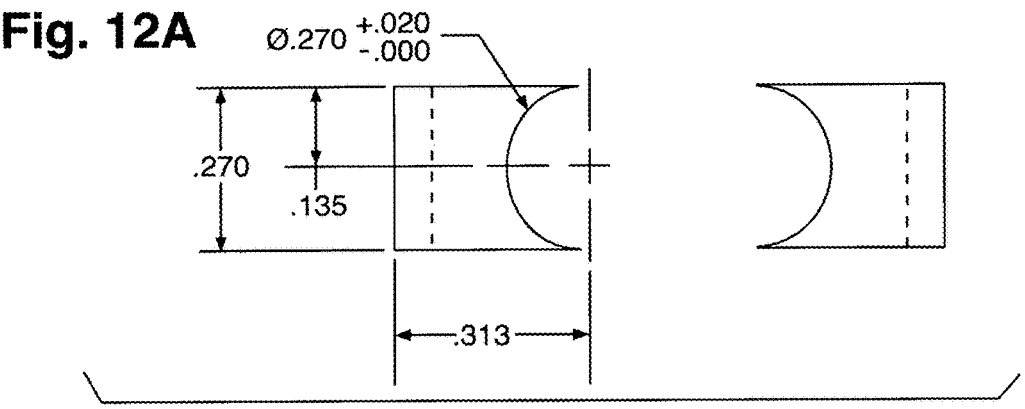
Figure 12B:
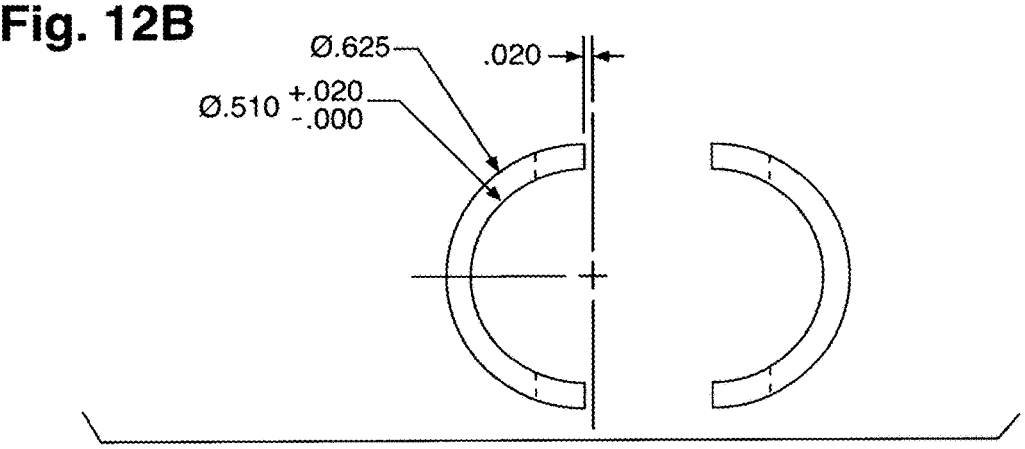
Figure 12C:
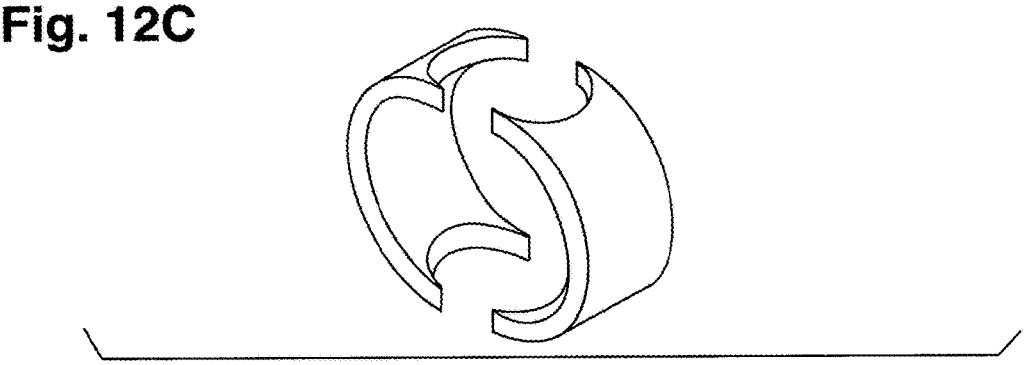

FIGS. 12A, 12B and 12C show several views of another grease sleeve/grease holder, clip version, with FIG. 12A being an exploded top view; FIG. 12B being an exploded elevational side view; and FIG. 12C being an exploded perspective view. It is in a form of a two-piece collar that, when incorporated with a falex pin and vee block device such as otherwise found within FIGS. 2 and 3, is secured with a U-shaped clip or a C-clamp type device akin in operation to well-known Vise-Grip pliers. As with the grease sleeve/grease holder of FIGS. 2, 3, 4A, 4B and 4C, although the material of the present two-piece version is, for example, #316 stainless steel, another material could be used such as another metal or alloy, a rubber, or a plastic.

Figure 13:
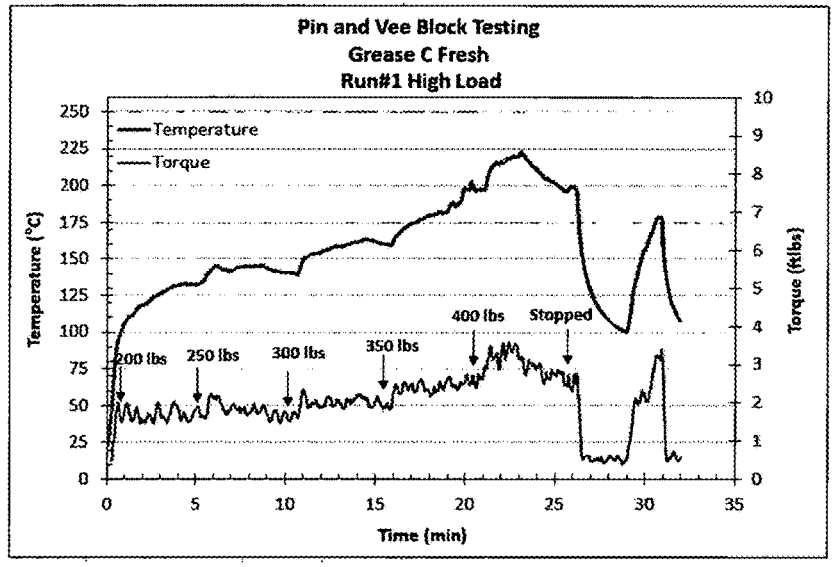
Figure 14:
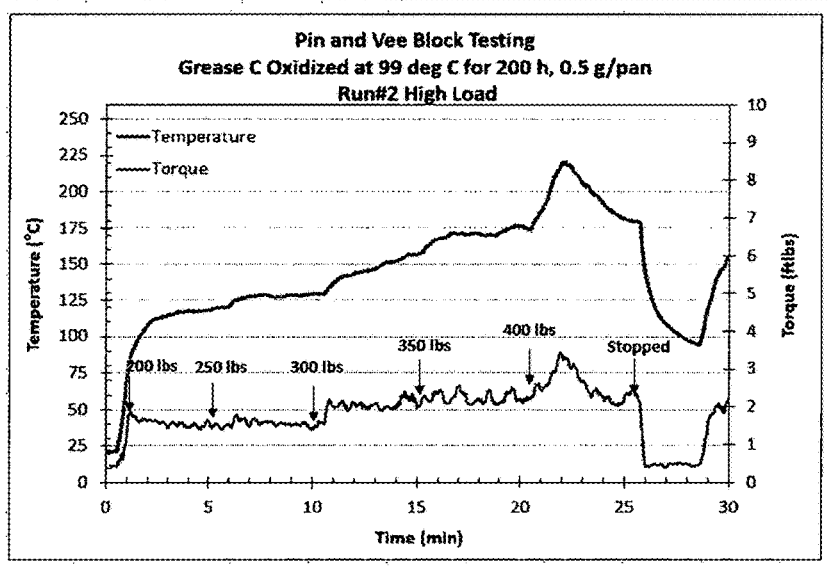

FIGS. 13 and 14 are graphs of falex pin and vee block wear testing, respectively with fresh and oxidized samples of Grease C.

Figure 15:
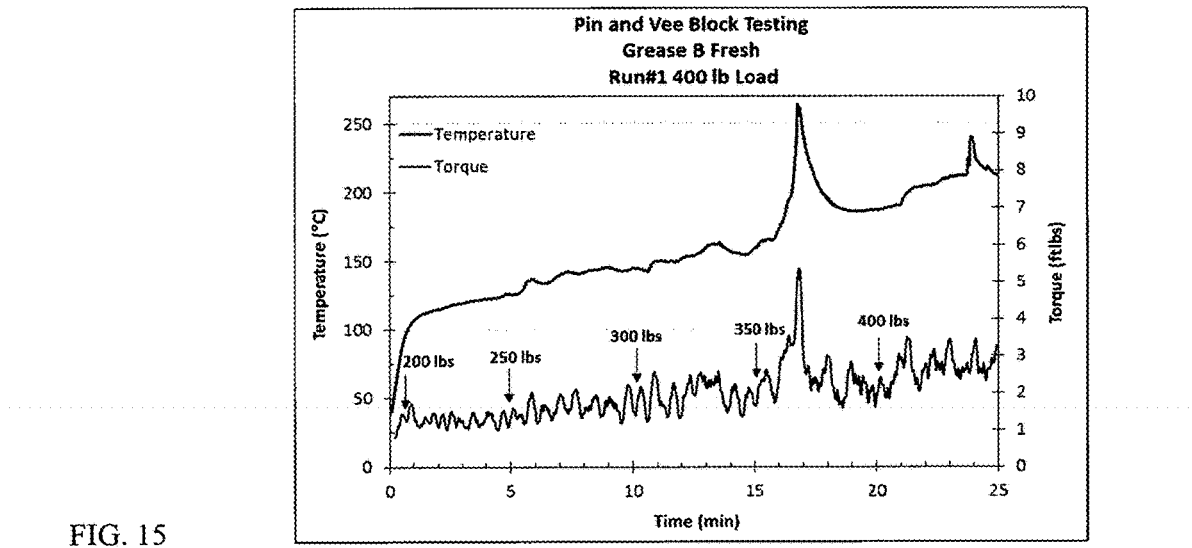
Figure 16:
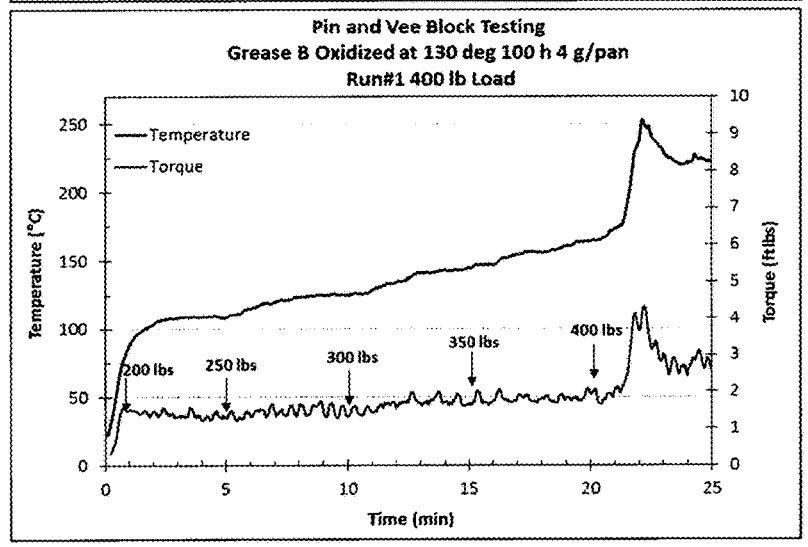

FIGS. 15 and 16 are graphs of falex pin and vee block wear testing, respectively with fresh and oxidized samples of Grease B.

Figure 17:
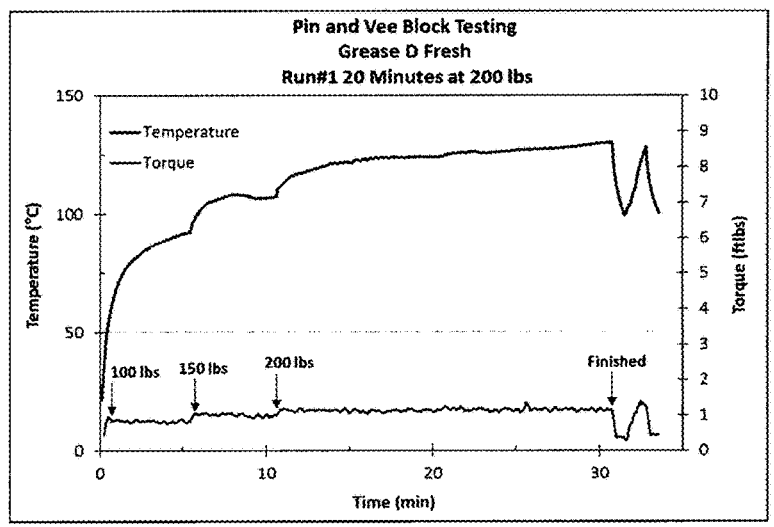
Figure 18:
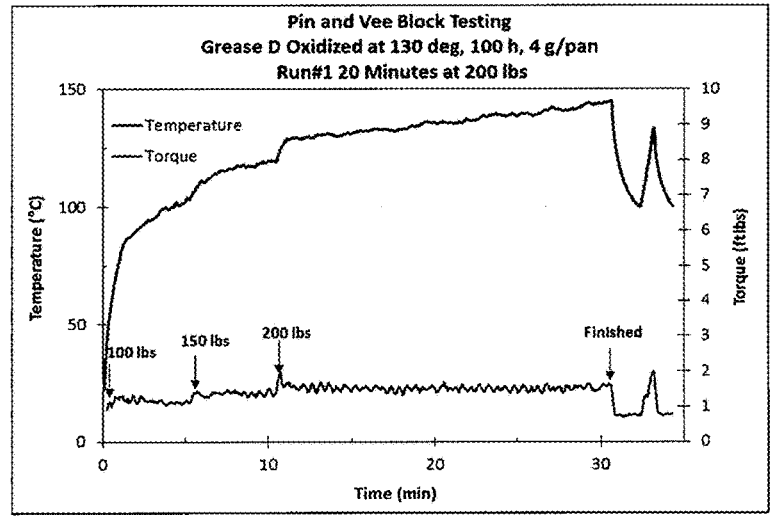

FIGS. 17 and 18 are graphs of falex pin and vee block wear testing, respectively with fresh and oxidized samples of Grease D.

Figure 19:
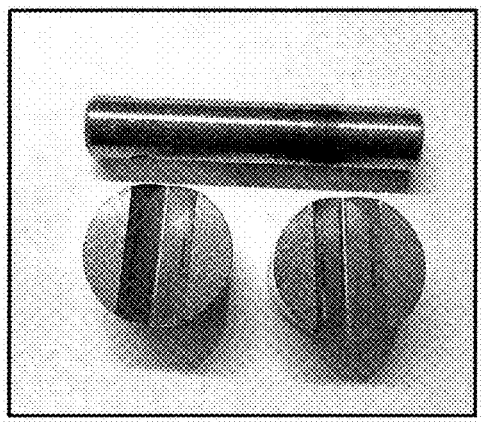
Figure 20:
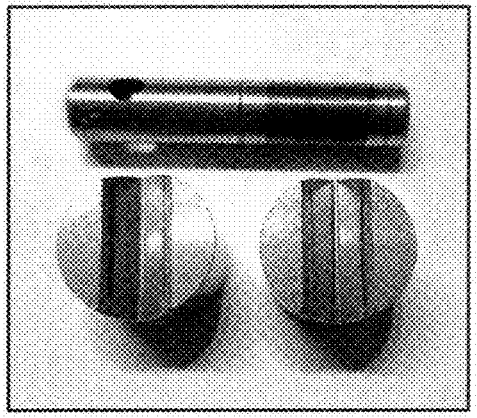

FIGS. 19 and 20 are views of falex pin and vee block parts upon falex pin and vee block testing, respectively with fresh and oxidized samples of Grease D. Note, FIGS. 17 and 18.

Figure 21:
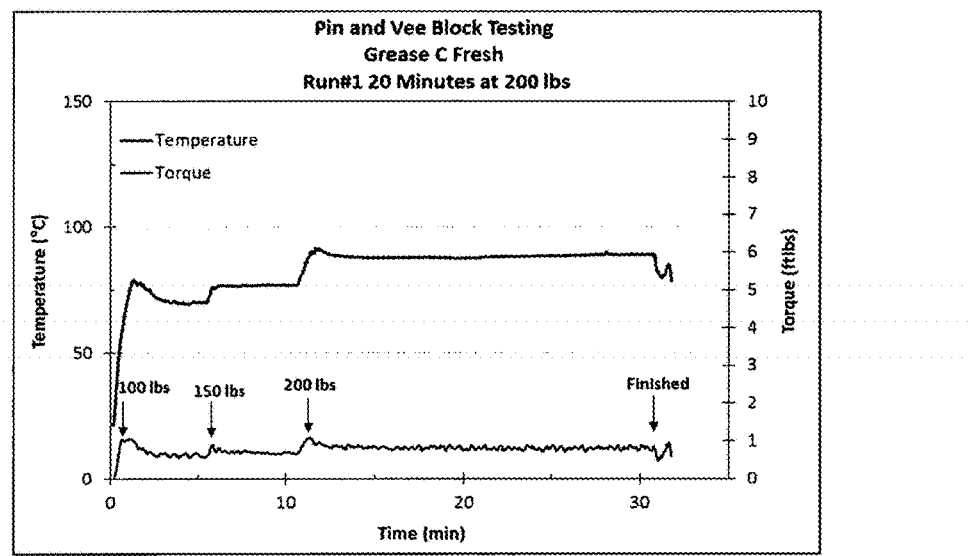
Figure 22:
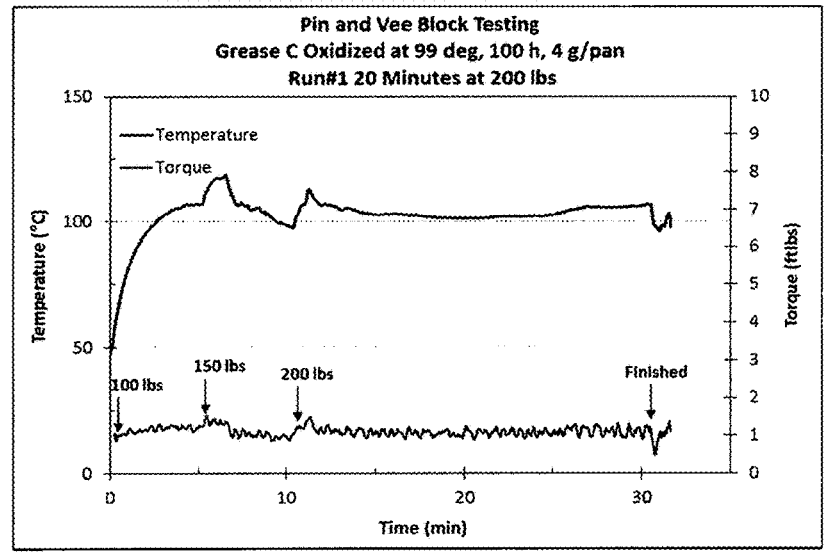

FIGS. 21 and 22 are graphs of falex pin and vee block wear testing, respectively with fresh and oxidized samples of Grease C.

Figure 23:
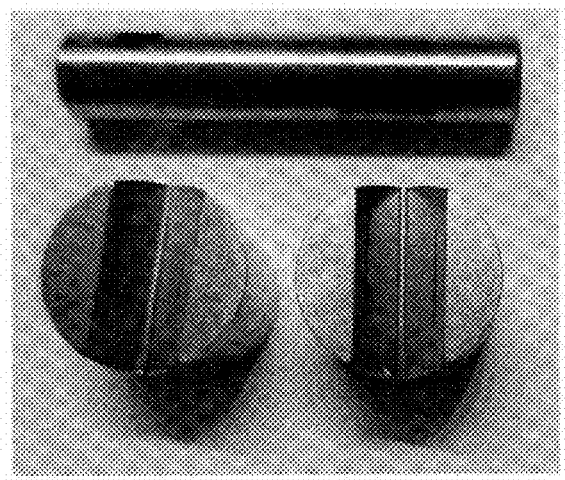
Figure 24:
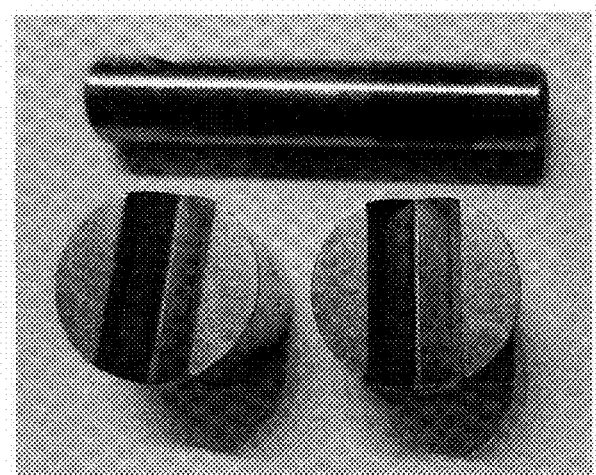

FIGS. 23 and 24 are views of falex pin and vee block parts upon falex pin and vee block testing, respectively with fresh and oxidized samples of Grease C. Note, FIGS. 21 and 22.

Figure 25:
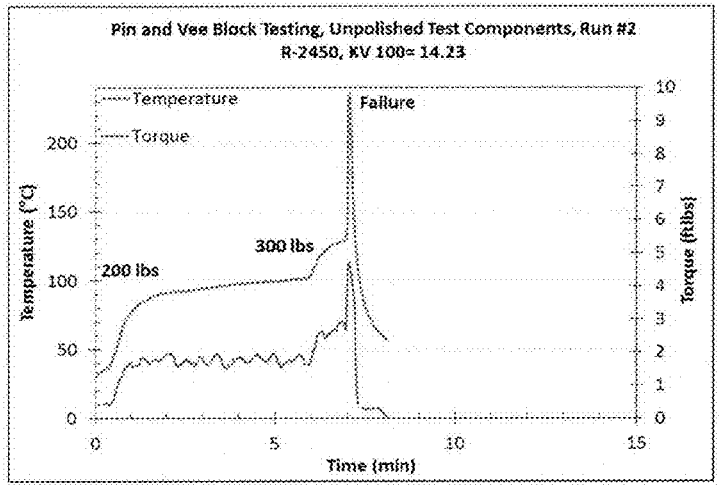

FIG. 25 is a graph of falex pin and vee block wear testing, with unpolished parts.

Figure 26:
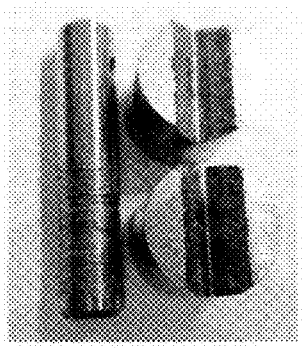

FIG. 26 is a view of falex pin and vee block parts upon falex pin and vee block testing with unpolished parts. Note, FIG. 25.

Figure 27:
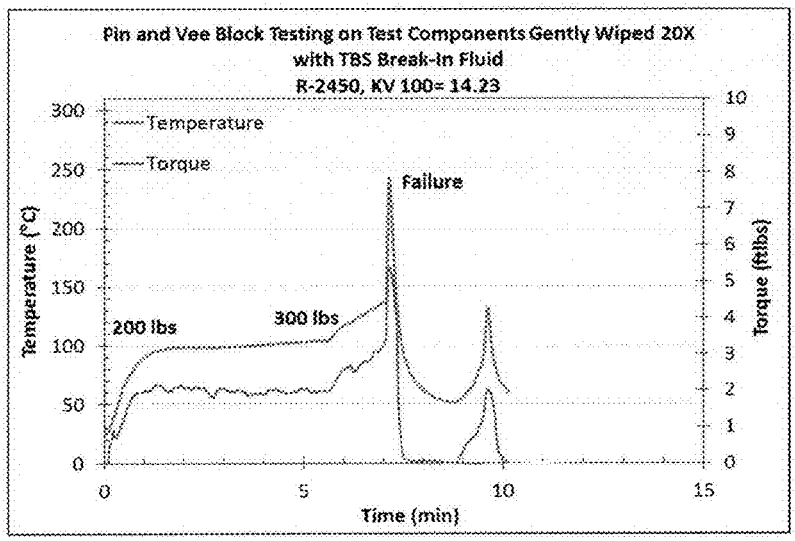

FIG. 27 is a graph of falex pin and vee block wear testing with polished parts.

Figure 28:
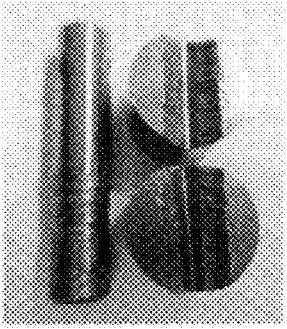

FIG. 28 is a view of falex pin and vee block parts upon falex pin and vee block testing with polished parts. Note, FIG. 27.

Figure 29:
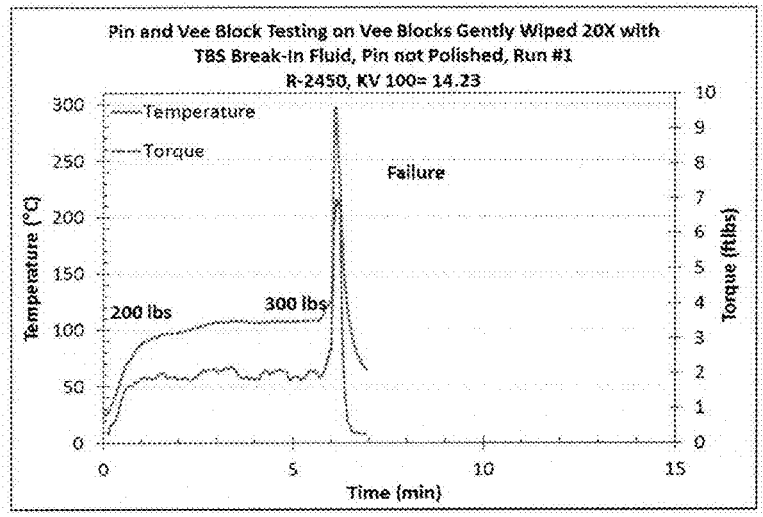

FIG. 29 is a graph of falex pin and vee block wear testing with polished vee blocks.

Figure 30:
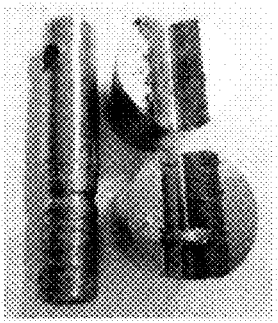

FIG. 30 is a view of falex pin and vee block parts upon falex pin and vee block testing with polished vee blocks. Note, FIG. 29.

Figure 31:
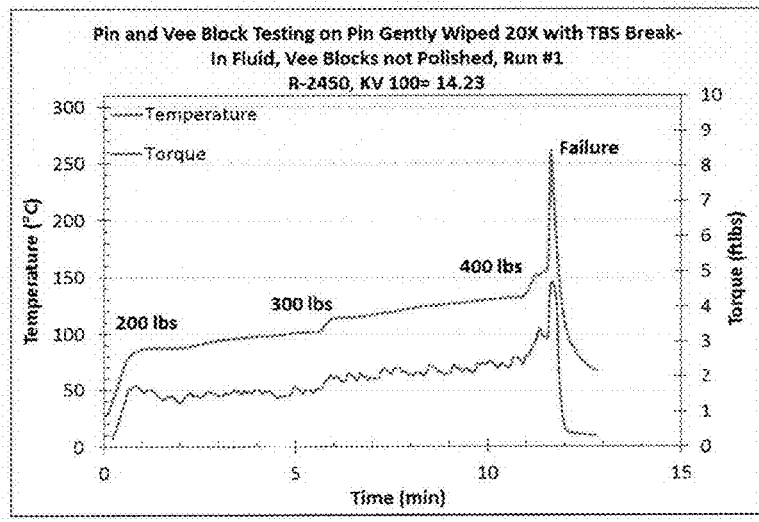

FIG. 31 is a graph of a first run of falex pin and vee block wear testing with polished falex pin.

Figure 32:
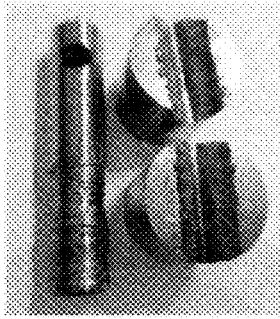

FIG. 32 is a view of falex pin and vee block parts upon falex pin and vee block testing with polished falex pin (first run). Note, FIG. 31.

Figure 33:
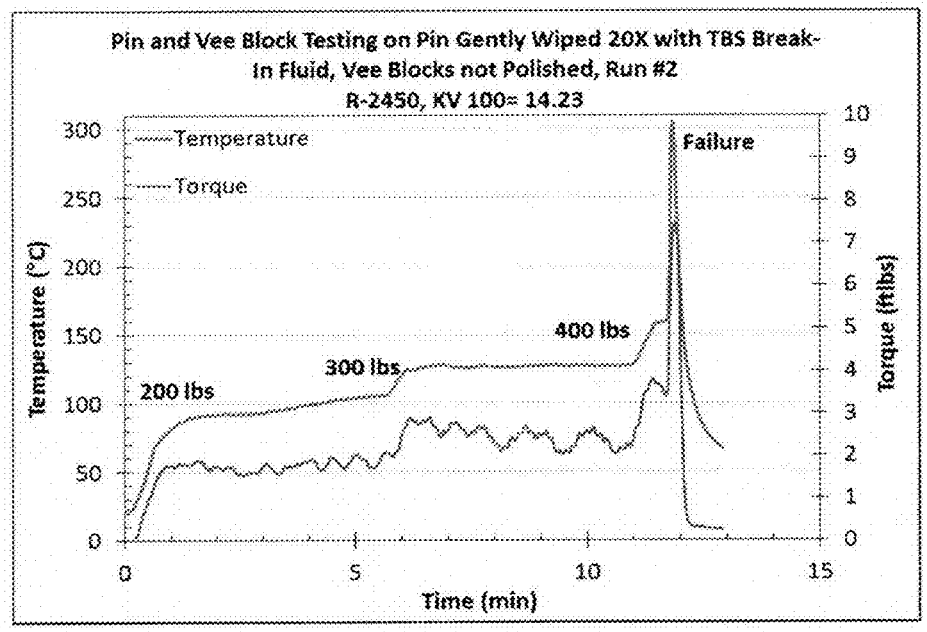

FIG. 33 is a graph of a second run of falex pin and vee block wear testing with polished falex pin.

Figure 34:
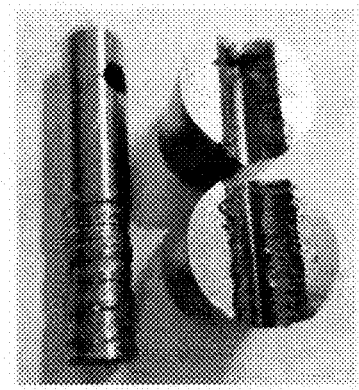
Figure 35:
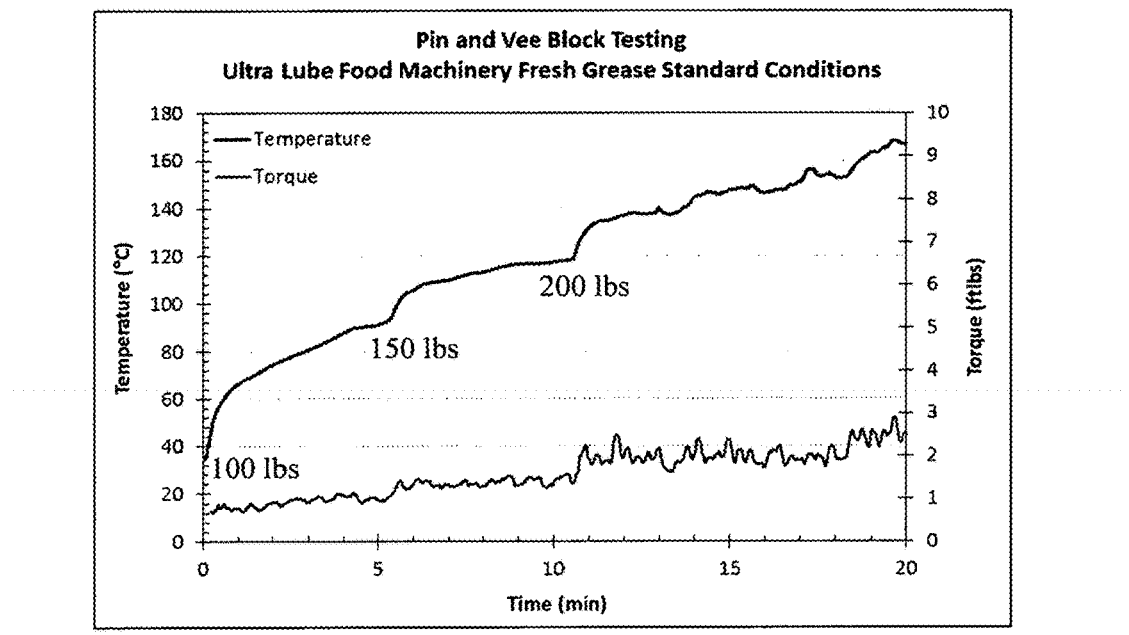
Figure 36:
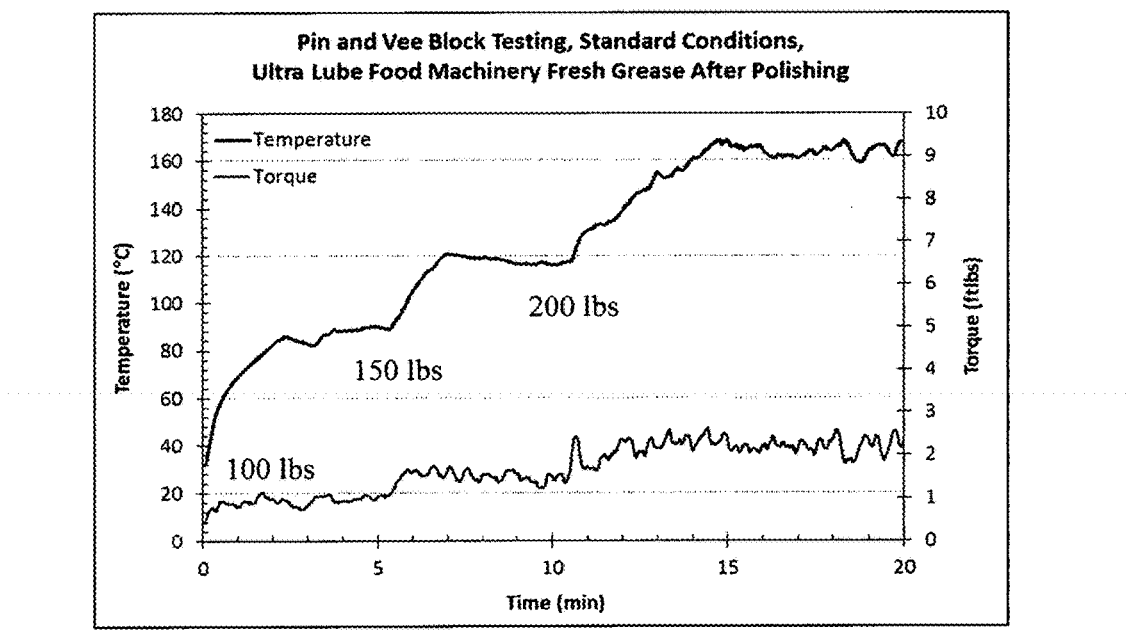
Figure 37:
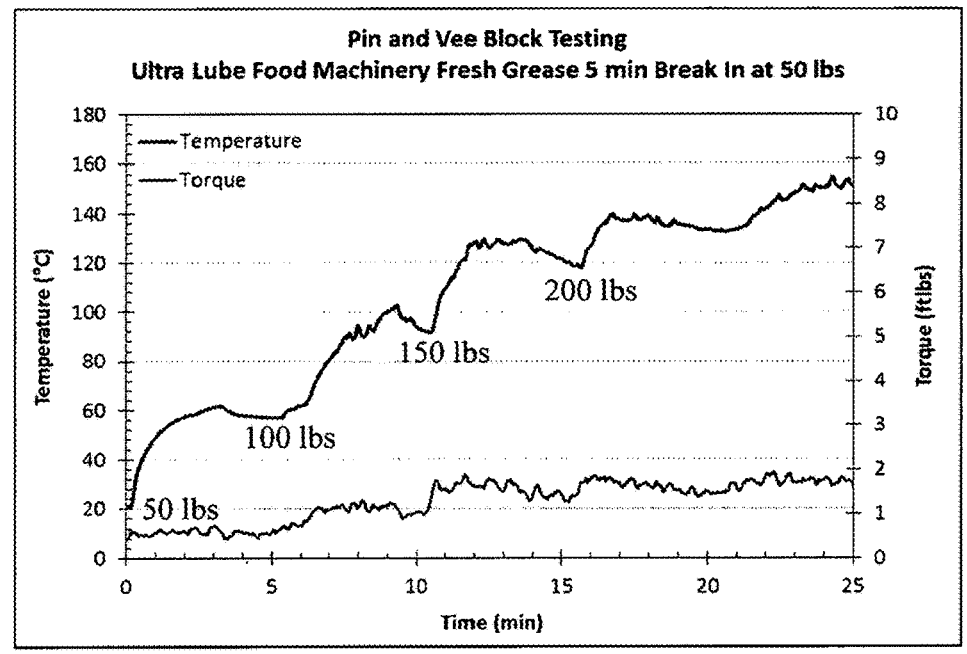
Figure 38:
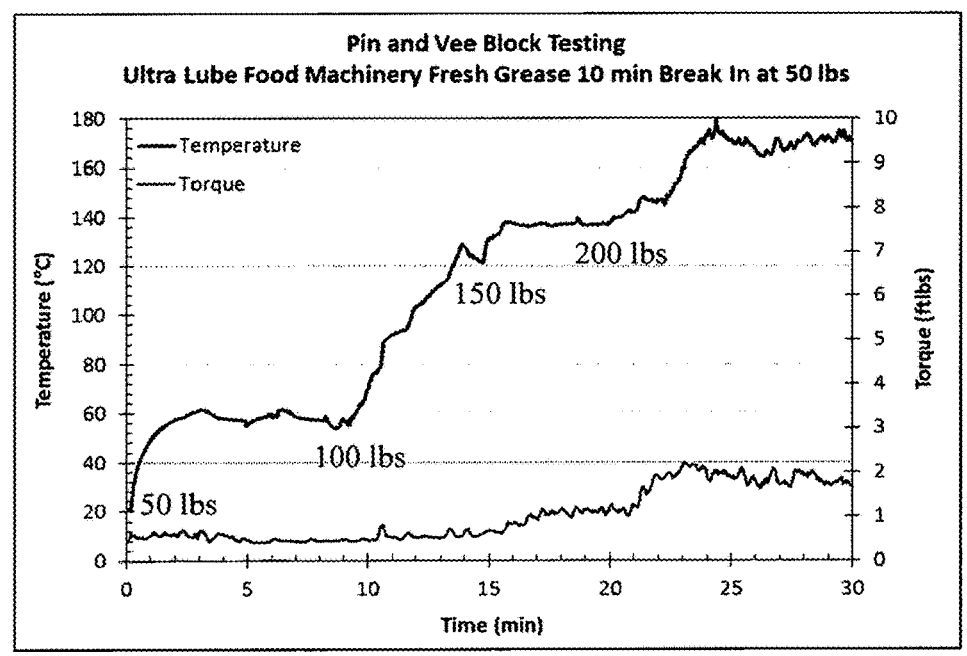
Figure 39:
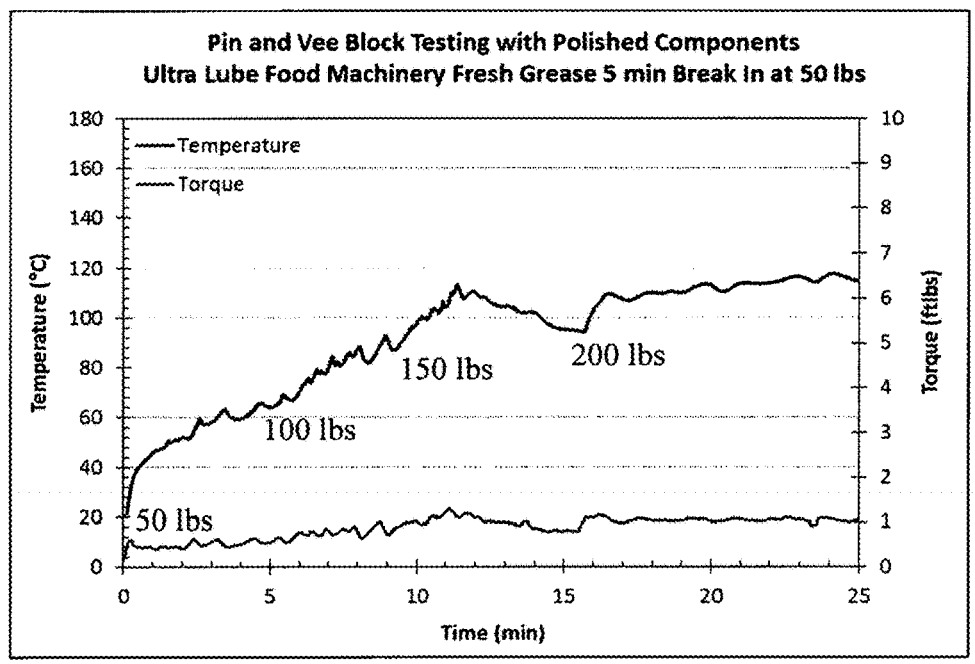
Figure 40:
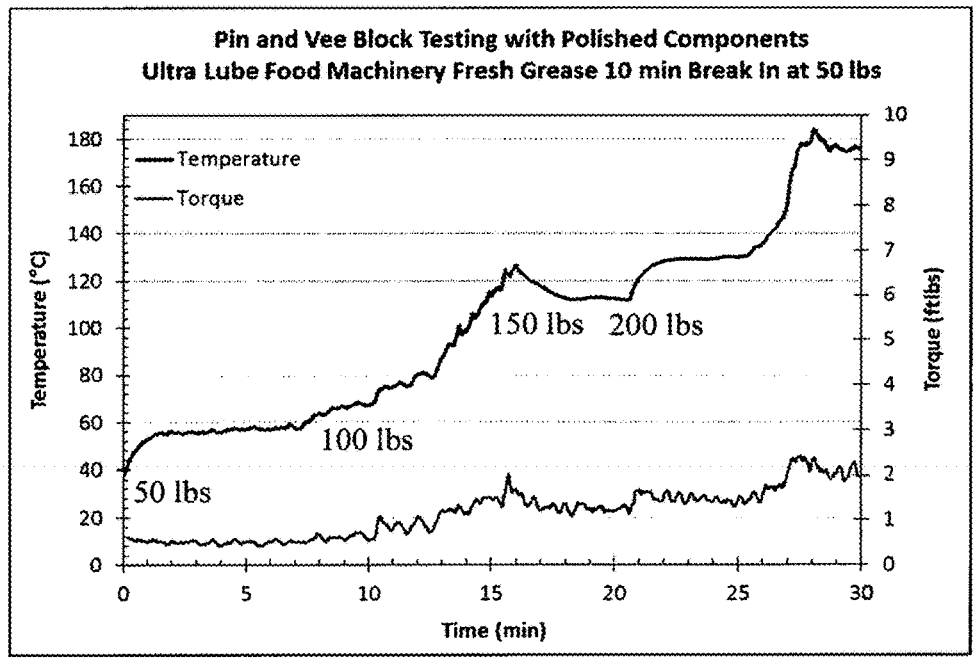
Figure 41:
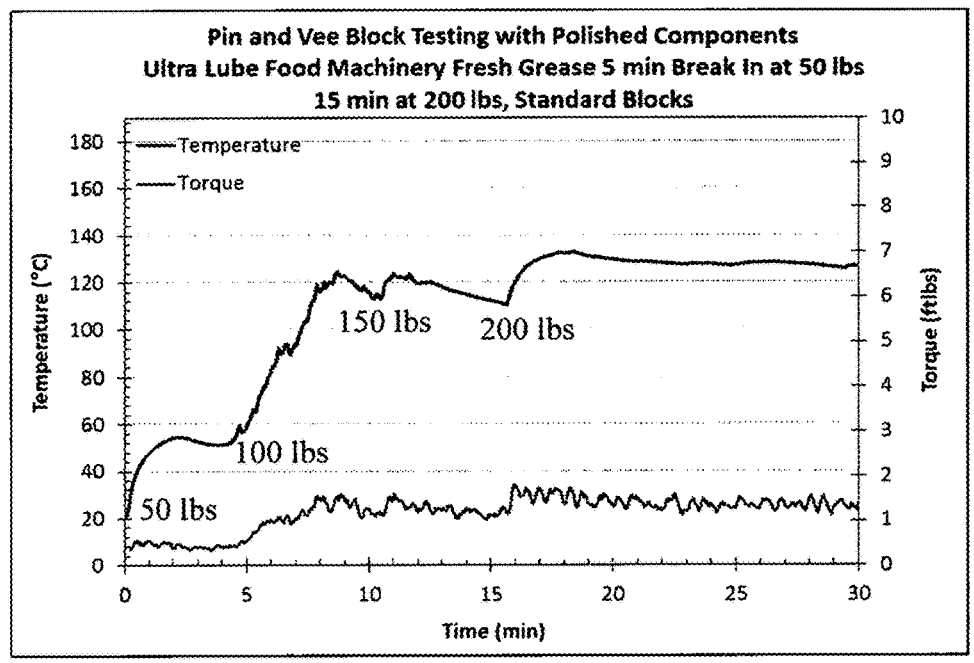
Figure 42:
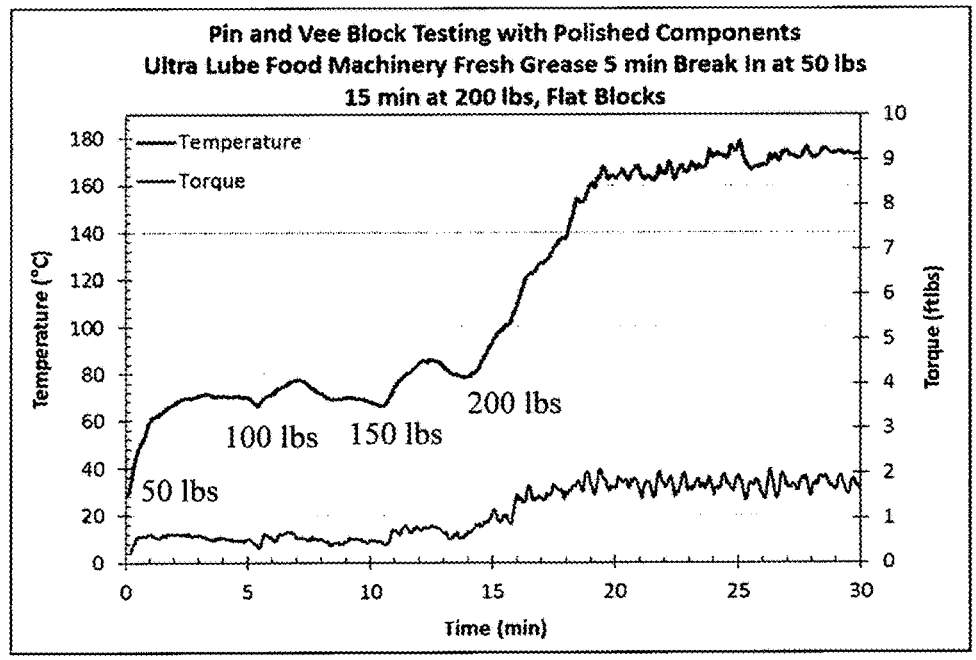

FIG. 34 is a view of falex pin and vee block parts upon falex pin and vee block testing with polished falex pin (second run). Note, FIG. 33.

FIGS. 35-42 graphs of falex pin and vee block wear testing runs with Grease A under various test parameters.

The invention can be further understood by the detail set forth below. As with the foregoing, the following, which may be read in view of the drawings, is to be taken in an illustrative, and not necessarily limiting, sense.

Wear testing and additional experimentation are illustrative of the invention.

Wear Testing

Grease oxidation testing as alluded to above, particularly in which a very small, 2.5-g test sample, distributed equally in five separate sample dishes, 0.5-g per dish, was tested in modified ASTM D942 type testing, set the platform for an investigation concerning the effects of grease oxidation on erosion of the wear protection level of a grease. For wear testing analysis of fresh and oxidized grease samples, several well-established grease wear test methods were considered, but all were determined to require much larger grease mass than the 2.5-g limit desired.

Thus, both Four-Ball wear test methods, i.e., regular Four-Ball ASTM D2266/DIN 51350 and Four-Ball EP ASTM D2596 methods, require approximately a 15-gram sample. In a somewhat extreme contrast, the Timken Method, i.e., the ASTM D2509 test method, requires a 900-g to 1400-g sample, which is obviously much too large a sample, even if one desires to evaluate the wear effects of an oxidized grease sample in the standard ASTM D942 method.

Figure 1A:
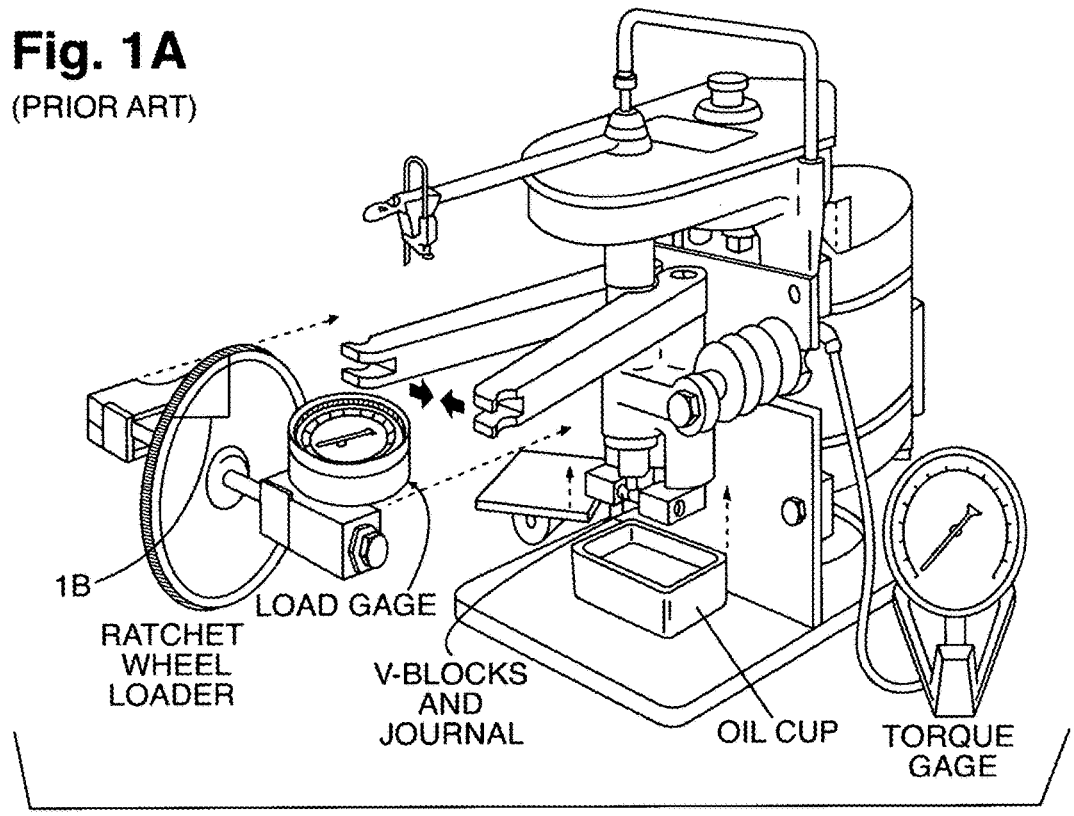
Figure 1B:
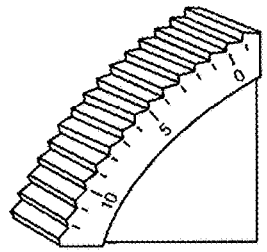

To the present inventors, however, the simple falex pin and vee block wear test provided a possible approach. The falex pin and vee block test apparatus such as shown in FIGS. 1A and 1B was developed early in the effort to evaluate lubricant wear resistance, in 1927. In 1967, the ASTM D2760 test method was approved.

It was apparent to the present inventors that, if the falex pin and vee block test machine as in FIGS. 1A and 1B was going to be suitable for measuring wear properties of the very small volume of test grease produced by the modified ASTM D942 mentioned above, then a means of presenting this smaller sample to the falex pin and vee block wear test equipment was needed. For that purpose, the present inventors conceived, designed, and made a special contrivance, which they termed the Grease Wear Test Device, also termed a grease sleeve or a grease holder, to be used with the falex pin and vee block test machine. See, FIGS. 2, 3, 4A, 4B and 4C. See also, FIGS. 12A, 12B and 12C. This new grease wear test device can be part of a modified falex pin and vee block device such as found within FIGS. 2 and 3. It provides for a grease wear test with a small grease sample held in place during testing.

The grease sleeve surrounds the falex pin and holds the opposing vee blocks in place, while ensuring that the chosen mass of grease is kept reasonably contained during the test. The assembled modified falex pin and vee block device, assembled with the grease holder, for example, as shown in FIG. 3, and containing, for example, about 0.45-0.5 grams of grease as determined by measuring the weight of modified falex pin and vee block device or the grease wear test device itself with and without the grease wear test sample.

After placing the falex pin and vee blocks of the modified falex pin and vee block device, along with the grease sleeve carrying the test grease, in their otherwise normal positions on the falex pin and vee block test machine, a thermocouple is inserted into the appropriate thermocouple well shown in FIG. 2. The grease sleeve provides for an inside cavity for the small sample of grease or other organic paste product to be tested.

Figure 5:
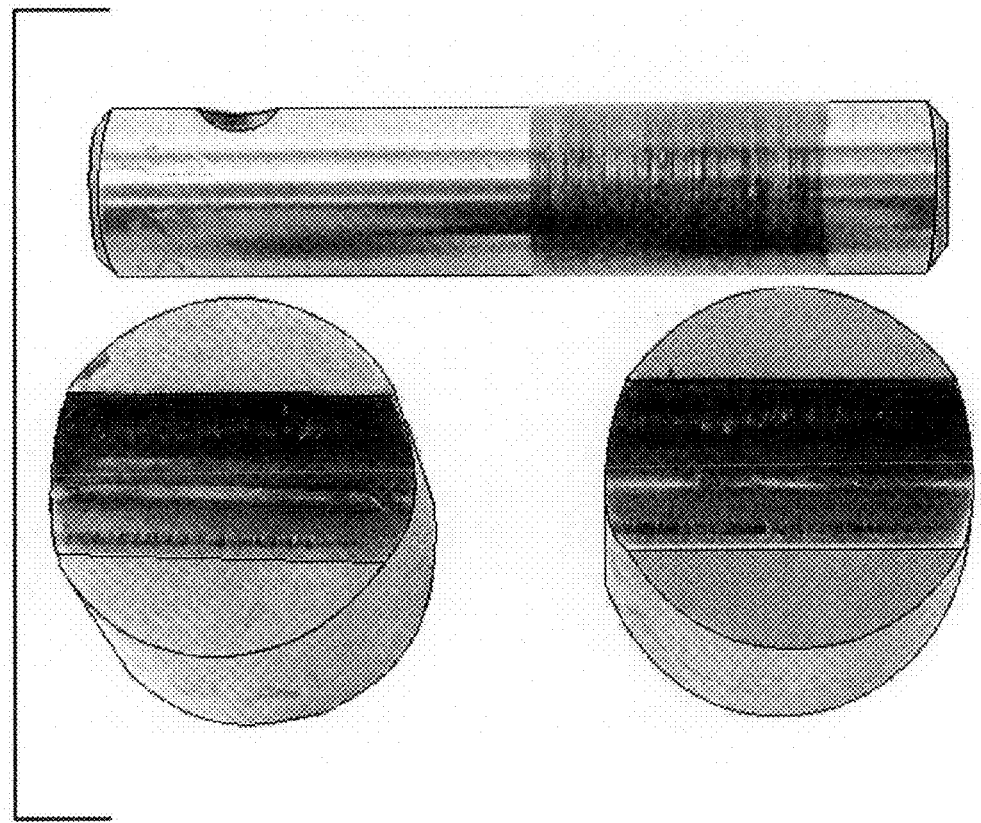
FIG. 5 is a view of a fresh falex pin and vee block wear scar, with Grease A.
Figure 6:
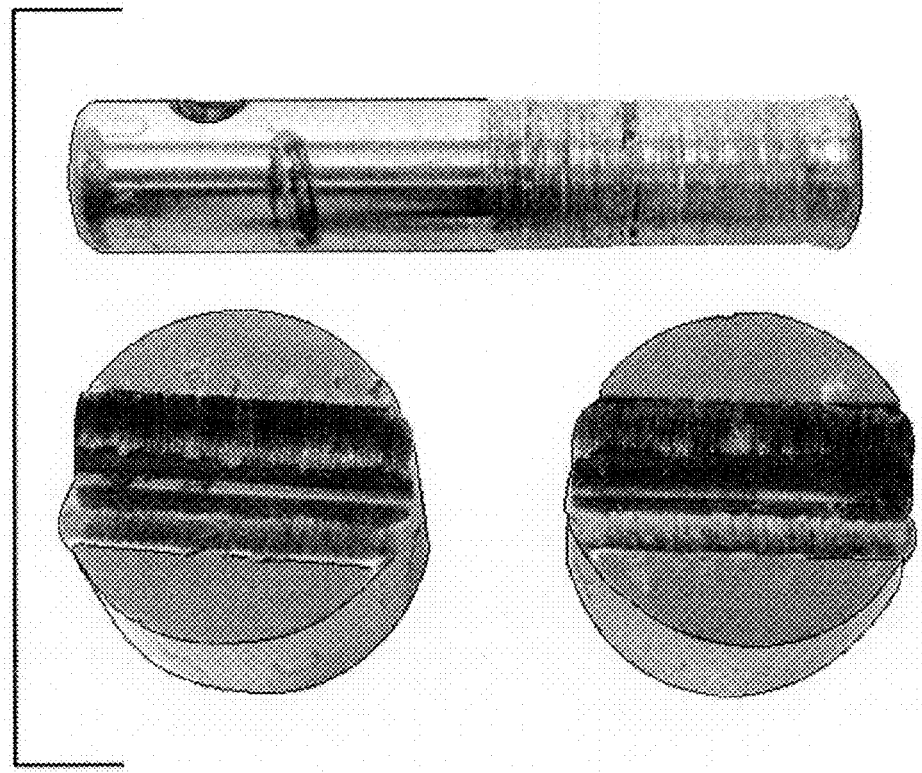
FIG. 6 is a view of an oxidized falex pin and vee block wear scar, with Grease A.

The test is performed by progressively applying a load to the V-blocks by its ratchet-wheel mechanism shown in FIG. 6. An initial 100-pound load is applied for five minutes, followed by an increase in load to a 150-pound value for another five minutes, and finally maintained at a 200-pound load for ten minutes. Throughout the test, the temperature of the falex pin and the torque exerted in overcoming friction by the vee block assembly are recorded and plotted. At the end of test, the falex pin is allowed to cool to 100° C., and the resulting wear is calculated as the number of teeth of the ratchet wheel mechanism that were advanced in order to maintain a constant load during the testing period. The wear value was determined by physical measurements and physics, with the value of a single tooth equalling 0.0018 mm of wear or 14.4108 teeth, equalling 0.001 of an inch of wear as taken from the Faville-LeVally Corporation operations manual. All wear data herein is reported as mm of wear. It is of interest to visually evaluate the falex pin and vee blocks for surface wear. Often, photographs taken of the wear scars on the falex pin and vee blocks are of interest. Compare, FIGS. 5 and 6, which show two different levels of wear on falex pins and vee blocks using the grease wear test device of FIGS. 2, 3, 4A, 4B and 4C, employed in the machine of FIGS. 1A and 1B without its standard pan for a liquid sample.

Wear protection for both fresh and oxidized samples of six greases was assessed by the present methodology employing the grease wear test device found in FIGS. 2, 3, 4A, 4B and 4C. The amount of wear shown by testing with the fresh grease compared to the grease in an oxidized state as generated in modified ASTM D942 testing, using a commercially available Quantum® instrument from Tannas Company, Midland, Mich., U.S.A., is compared. Both fresh and oxidized test samples of each grease are exposed to the final 200-lb. load applied for a 10-minute period through the vee blocks to the grease-lubricated falex pin. Tabulated data follows:

TABLE

Modified Falex Pin and Vee Block Device Grease Wear Testing

| Grease | Base Stock/ Thickener | Recommended Operating Temperature | Wear (mm) at 200 lbs. (Fresh) | Wear (mm) at 200 lbs. (Oxidized at 99° C.) |
|---|---|---|---|---|
| A | Bio (soy)/ Aluminum | 0° C.-215° C. | 0.041 ± 0.0 | 0.235 ± 0.028[A] |
| B | Bio (soy)/ Aluminum | −30° C. 149° C. | 0.018 ± 0.0018 | 0.030 ± 0.001[B] |
| C | Synthetic ester/ Lithium | −40° C.-120° C. | 0.021 ± 0.0018 | 0.023 ± 0.007 |
| D | Bio (canola)/ Aluminum | −23° C.-188° C. | 0.025 ± 0.0053 | 0.026 ± 0.0018 |
| E | Mineral (Lithium Complex) | −23° C.-204° C. | 0.037 ± 0.0035 | 0.035 ± 0.0018 |
| F | Mineral (Lithium Complex) | −12° C.-163° C. | 0.028 ± 0.0 | 0.028 ± 0.0035 |

[A]Data at 100-lb. value, test failure at 200-lb. value
[B]Data for ASTM D942 oxidized sample at 130° C.

Among the fresh greases in these tests, fresh Grease A, the bio-based soy grease with an aluminum-compound thickener, was found to show the most wear when tested using the present methodology. The test showed a wear depth of 0.041 mm. In comparison, the other five fresh greases ranged from 0.018 to 0.037 mm in wear.

Regarding the oxidized versions of these greases, the Table shows some interesting comparisons. Oxidized Grease A shows nearly six times more wear after exposed to oxidation conditions than its fresh counterpart, and, as will be discussed subsequently, further wear was protectively blocked by the grease sear test device. Four of the six greases, Greases C, D, E and F, show essentially no oxidation effect.

Even more informative and explicit information was simultaneously generated during these wear tests. That is, as previously mentioned, the torque produced by friction resisting rotation of the Pin and the internal temperature of the falex pin produced by this friction was continuously recorded. Recorded results on the fresh sample of Grease A are found in FIG. 7.

Figure 7:
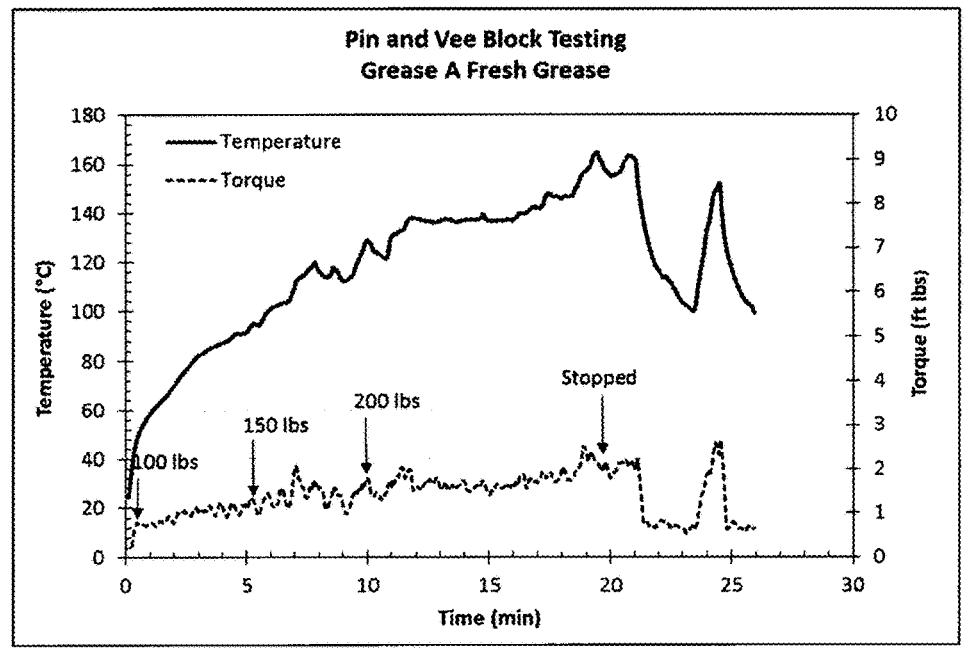
FIG. 7 is a graph of falex pin and vee block wear testing, fresh Grease A sample.

FIG. 7 shows both the torque and temperature experienced by the falex pin until the end of the test. As shown, the temperature of the falex pin rises rapidly as a consequence of friction of the vee blocks pressed against the falex pin by the loads indicated. Variation of torque values shown in the torque trace are believed to reflect the wear process occurring: peaks indicate a momentarily higher level of contact and metal removal from falex pin and/or vee block.

Figure 8:
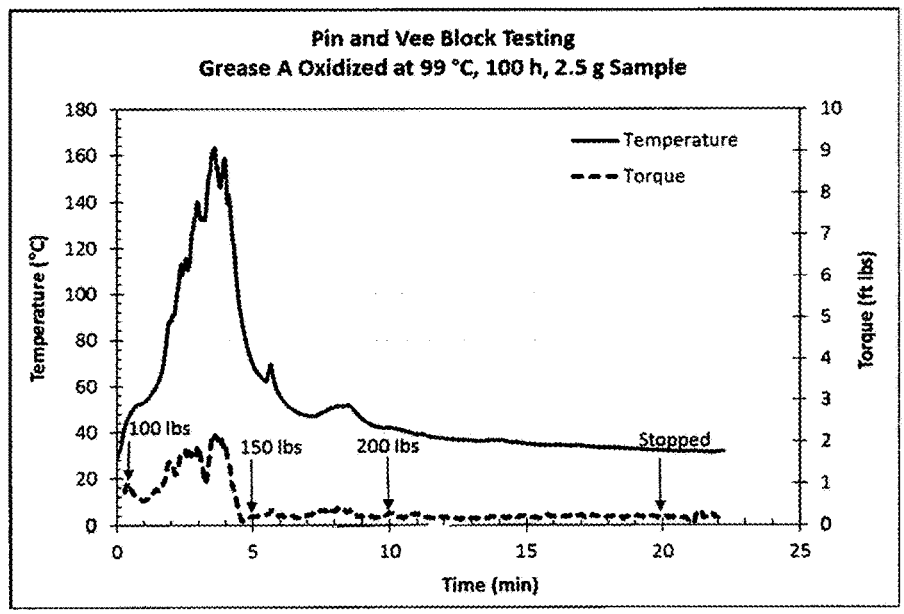
FIG. 8 is a graph of falex pin and vee block wear testing, oxidized Grease A sample.

In contrast, FIG. 8 shows the effect of the modified oxidation previously discussed in this paper on the wear response in the falex pin and vee block test using the special grease wear test device. The extent of the rapid temperature rise and the rapid rate of wear metal removal from the falex pin and vee block led to the protection of the collar of the grease wear test device at a mere 100-lb. load. This, of course, ended the wear test and any related further wear. Thus, the recorded wear of 0.235 mm was only a portion of that that would have occurred had the protective collar not been incorporated.

Figure 9:
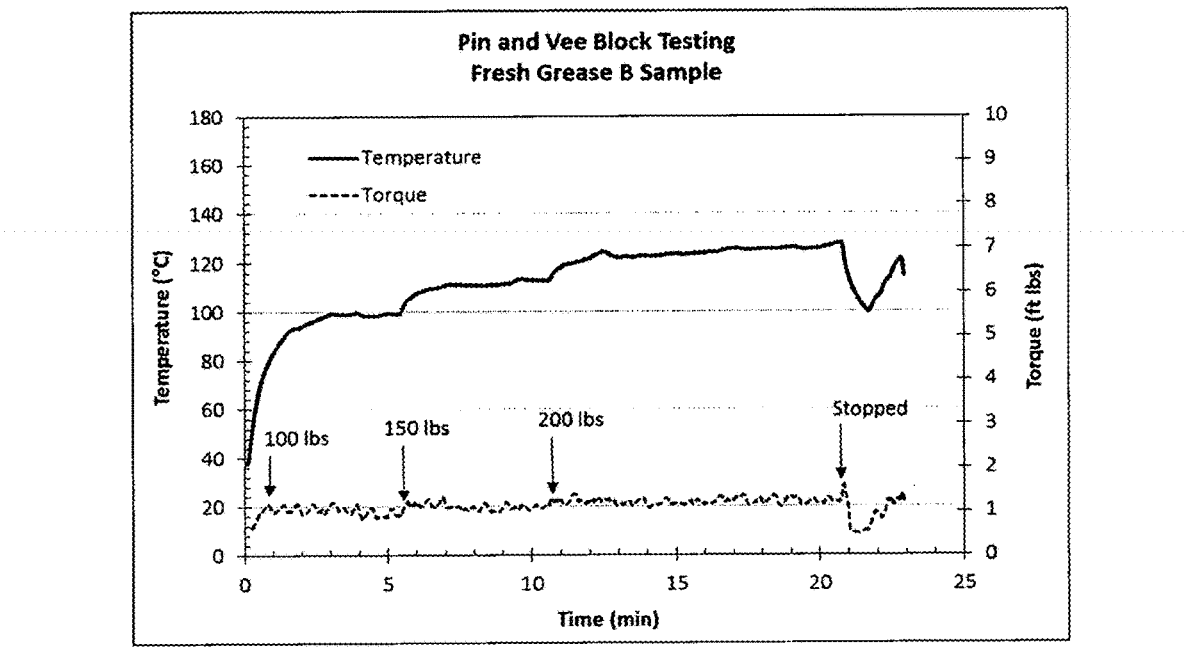
FIG. 9 is a graph of falex pin and vee block wear testing, fresh Grease B sample.
Figure 10:
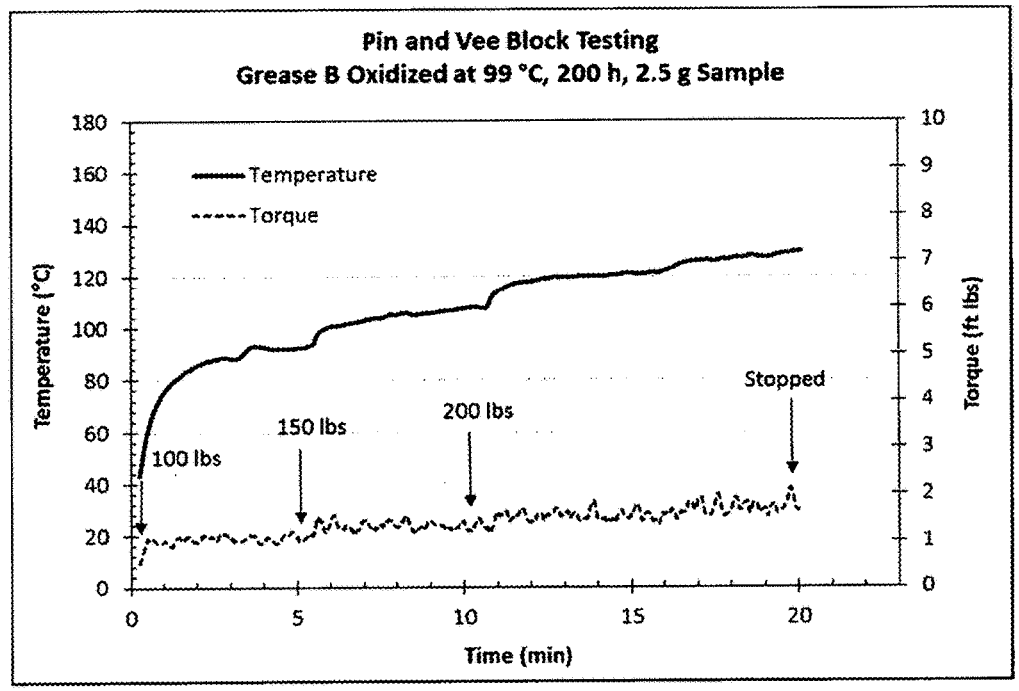
FIG. 10 is a graph of falex pin and vee block wear testing, oxidized Grease B sample.

In contrast, fresh Grease B, also a bio-based soy grease with an aluminum-compound thickener, was found to behave considerably differently than fresh Grease A. For example, as shown in FIG. 7, fresh Grease A during testing yielded a progressive increase in the torque over the test duration which resulted in an average wear diameter loss of 0.041 mm. However, as shown in FIG. 9, fresh Grease B, while giving a slight stepwise and subsequently constant response to increasing load, exhibited in an average wear loss of 0.018 mm. This form of response of oxidized Grease B remained the same but at a somewhat higher level of torque response to increase in load as shown in FIG. 10. Moreover, wear of the oxidized Grease B, 0.030 mm, was about double its fresh test level of 0.018 mm.

Figure 11:
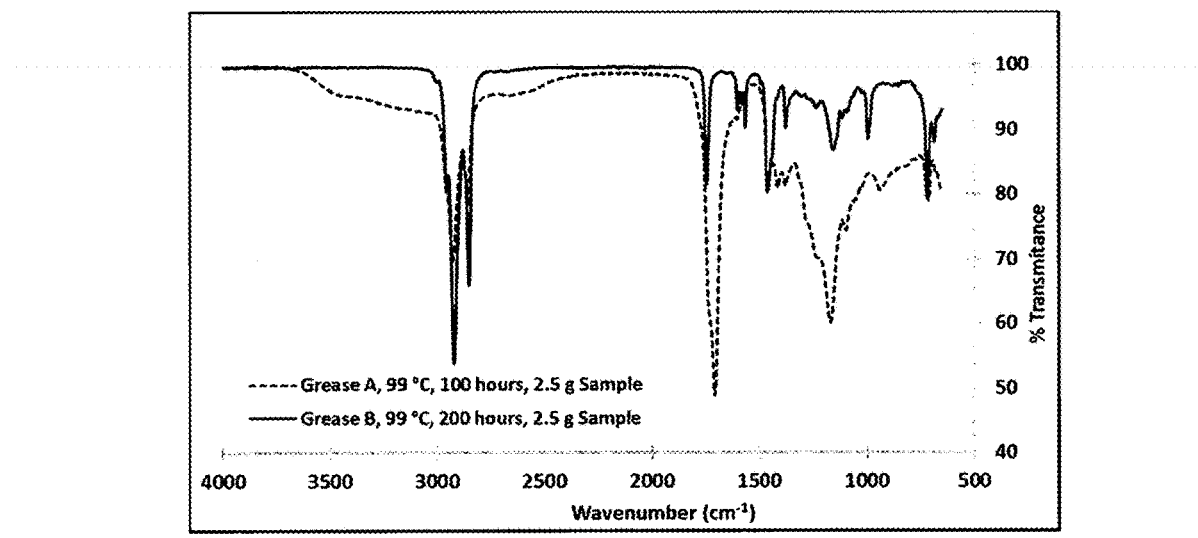
FIG. 11 is a graph of ATR-FTIR spectra of Greases A and B, both from modified ASTM D942 testing at 99° C. with a 2.5-g sample (0.5-g per dish) in which Grease A was subject to a 100-hour period, and Grease B to a 200-hour period.

The use of infrared spectroscopy is of considerable advantage in determining the extent of oxidation particularly when compared to other infrared spectra. For example, in FIG. 11, the infrared analysis of an oxidized sample of Grease B from an oxidation test at a 200-hour duration at 99° C. showed a much smaller increase in the signal strength at the wavenumbers between approximately 1700-1750 $cm^{-1}$ relative to that observed for Grease A also at 99° C. at a 100-hour time, even though the exposure time was doubled.

It is also worth noting that the new grease wear method shows reasonably good sensitivity. It is able to distinguish the wear resistance difference between a fresh grease and a partially oxidized grease in those cases where oxidation has affected the grease's wear resistance.

Biodegradable Grease C, a synthetic ester/lithium-compound thickened grease, and the bio-based Grease D, a canola based/aluminium-compound thickened grease, which are both reasonably oxidative resistant greases, gave similar wear test results. Wear testing revealed that Greases C and E performed as well as mineral-based Greases E and F. It should be noted that fresh bio-base Grease B was found to perform better in this new small scale wear testing method than either of the mineral-based greases. However, it was apparent that oxidation of Grease B reduced its wear preventive capability.

Additional Experimentation

Determining Maximum Load:

An experimental high load falex pin and vee block testing experiment was conducted using Mobil SHC Grease (Grease C) which had been oxidized at 99° C. for 200 hours at 0.5 g of sample per pan. The load steps (each 5 minutes in duration) were 200 lbs., 250 lbs., 300 lbs., 350 lbs., and 400 lbs. At the 400-lb. load, the grease was observed to break, with an abrupt temperature rise followed by a temperature drop, and a wear tooth count of 25. A moderate amount of surface wear was observed on the vee blocks. The experiment was repeated once with similar results, with a failure at 400 lbs. but 30 teeth of wear. The same step method up to 400 lbs. was followed using the fresh grease. Tooth wear counts of 29 teeth and 27 teeth at 400 lbs. were observed for the two fresh grease runs. Note, FIGS. 13 and 14. There was no significant difference in wear scarring between fresh and partially oxidized grease under these conditions.

One thing noticed with Grease C, which is a temperature-sensitive grease with an upper temperature limit of 120° C., is that at least some part of the falex pin and vee block failure was phase change related. An unusual odor was present during the failure; and when the system was taken apart, present were drops of liquefied grease, which had changed color from ivory to black in the support tray. Very little grease remained in the holder ring.

This indicates that caution should be exercised when pushing some greases to operational limits or else failure occurs. Also, for this grease, no apparent differences in wear count are observed for the fresh versus the oxidized grease whether tested at 200 lbs. or 400 lbs. of force.

Also, an experimental high load falex pin and vee block testing experiment was conducted using Renewable Lubricants biodegradable EP grease (Grease B) which had been oxidized at 130° C. for 100 hours at 4 g of sample per pan. The load steps (each 5 minutes in duration) were 200 lbs., 250 lbs., 300 lbs., 350 lbs., and 400 lbs. At the 400-lb. load, the grease was observed to break, with an abrupt rise in temperature followed by a temperature drop. The wear tooth count at 400 lbs. was 35. The same step method up to 400 lbs. was followed using fresh grease. A tooth wear count of 41 teeth at 400 lbs. was observed for the fresh grease run. Note, FIGS. 15 and 16. Thus, no significant difference in the wear scarring between fresh and partially oxidized grease occurred under these conditions. In both cases, there was a drastic rise in temperature around 350-400 lbs., followed by a temperature drop typical of failure.

Melting of Grease B, color change to black, and an unpleasant odor were observed under these high load conditions. This generally compared to Grease C as noted directly above.

To summarize, every fresh and oxidized tested using the step method taken up to 400 lbs. broke, melted, and showed similar wear characteristics. These conditions appear to be too harsh for greases, and have not provided much meaningful information about their wear properties.

Accordingly, alternative wear conditions may be applied if unsatisfactory results are obtained, for example, by using the step method going up to 200 lbs. An increase in the time of load application at 200 lbs. may be employed to increase severity, rather than trying to increase load amount.

Increasing Time at 200 lbs. Load:

Noting that increasing force load was not the most effective strategy for broadening the wear difference between fresh and oxidized greases, with all tested greases breaking uncontrollably, an experiment was run where the time of incubation at 200 lbs. was increased to 20 minutes. LPS Thermaplex grease from canola (Grease D), fresh and oxidized at 130° C. for 100 hours, was chosen for the test because it had shown significant oxidation at this temperature without melting, but showed no statistically significant difference in wear when tested for 10 minutes at 200 lbs. When held at 200 lbs. for 20 minutes, the tooth wear count was 8 teeth for the fresh grease and 23 teeth for the partially oxidized grease. An increased temperature and torque response was also observed with time with the oxidized grease. In addition, even though no break occurred, a longer and deeper wear scar was observed on the Vee Block from the oxidized grease run. Note, FIGS. 17-20.

Thus, holding for the extended time period of 20 minutes at 200 lbs. may enable better differentiation between the wear properties of fresh and oxidized greases. Testing with another grease may prove helpful in rendering a more useful generalization regarding the increased sensitivity observed by this methodology.

And so, another grease, a synthetic ester type grease (Grease C) was tested. It is a stable grease showing very mild oxidation at 99° C. for 100 hours and no difference in the falex pin and vee block wear testing conditions (10 minutes at 200 lbs.) reported elsewhere. As observed with Grease D from canola, extension of the time at 200 lbs. to 20 minutes with Grease C allowed observation of a more measurable difference between tooth wear for oxidized grease (10 teeth) versus fresh grease (5 teeth). In addition, the temperature profile for the oxidized grease was significantly elevated, and a slightly wider and longer wear scar was observed on the vee blocks remaining after the oxidized Grease C wear testing. Note, FIGS. 21-24.

This experiment supports the use of this modified set of conditions (5 minutes at 100 lbs., 5 minutes at 150 lbs., 20 minutes at 200 lbs.) for analyzing wear differences between fresh and partially oxidized samples of grease. Other milder load and extended time conditions may be employed to effect. For instance, a milder load may be no more than about 250 lbs. or 300 lbs.

Studying Effect of Polishing Metal Components:

An in-depth study of the effect of polishing with break-in fluid for tapered bearing simulator (TBS) instruments (U.S. Pat. No. 4,445,365 to Selby and U.S. Pat. No. 5,565,621 to Selby et al.) on a diaper cloth on individual components of the falex pin and vee block system was conducted. The R-2450 base oil (KV 100 of 14.23) was used for these tests because it has proven in the past to be sensitive to the effects of this polishing procedure. The following conditions were compared using the 5-minute stepwise falex pin and vee block method noted above:

No polishing (cyclohexane rinse of test components only). Note, FIGS. 25 and 26.

Polishing of vee blocks and falex pin. Note, FIGS. 27 and 28.

Polishing of vee blocks only. Note, FIGS. 29 and 30.

Polishing of pin only (repeated twice). Note, FIGS. 31 and 32, and 33 and 34.

As previously observed, a smoothing out effect on the torque trace appeared when the components were polished. This smoothing out effect seemed to be more pronounced when either all components or the vee blocks were polished, as opposed to just the falex pin. An unusual response to just the falex pin being polished occurred, and it happened twice (experiment repeated owing to the surprising outcome). When only the falex pin was polished, the system was able to withstand force up to 400 lbs., as opposed to only 300 lbs. as was the case in the experiments with the unpolished, all parts polished, and vee blocks only polished. The final diameters of the falex pins were smaller.

Additional Falex Pin and Vee Block Studies:

Various break-in and pretreatment conditions for the falex pin and vee block were evaluated using fresh Ultra Lube food machinery grease (Grease A). The following conditions were employed:

Standard falex pin and vee block grease protocol (5 minutes at 100 lbs., 5 minutes at 150 lbs., 10 minutes at 200 lbs.). Note, FIG. 35.

Pre-polishing of test components with TBS break-in fluid, then the standard falex pin and vee block grease protocol. Note, FIG. 36.

5 minutes at 50-lb. load, followed by the standard falex pin and vee grease protocol. Note, FIG. 37.

10 minutes at 50-lb. load, followed by the standard falex pin and vee block grease protocol. Note, FIG. 38.

Results were variable, which could be due to the age of the grease or variability of the test method. The 5-minute break-in at the 50-lb. load appeared to reduce the wear scar and temperature elevation. In contrast, the 10-minute break-in at the 50-lb. load appeared to increase both properties. Polishing the test parts with the TBS break-in fluid resulted in a smoother torque profile, as had been previously observed with this pretreatment procedure. This appeared to be the case even more when including a break-in period at the 50-lb. load.

The following wear scar measurements were observed:

Wear Scar Measurements

| Condition | Wear Scar |
| --- | --- |
| Grease A, standard conditions | 0.041 mm |
| Grease A, polishing test components, standard conditions | 0.033 mm |
| Grease A, break-in at 50 lbs. for 5 minutes | 0.028 mm |
| Grease A, break-in at 50 lbs. for 10 minutes | 0.058 mm |

Again, using fresh Grease A, various further break-in and pretreatment conditions for the falex pin and vee block were carried out. The following conditions were evaluated:

Pre-polishing of test parts with TBS break-in fluid, 5 minutes at a 50-lb. load, followed by the standard falex pin and vee block grease protocol. Note, FIG. 39.

Pre-polishing of test parts with TBS break-in fluid, 10 minutes at a 50-lb. load, followed by the standard falex pin and vee block grease protocol. Note, FIG. 40.

As seen before, breaking-in at the 50-lb. load leads to a smoother torque profile. The effect appeared more pronounced with the 5-minute break-in period, which also was observed to result in a lower endpoint temperature and less wear. The combination of polishing and breaking-in at the 50-lb. load gave the smoothest results.

The following wear scar measurements at a 200-lb. load were also observed:

Wear Scar Measurements at 200 lbs.

| Condition | Wear Scar |
|---|---|
| Grease A, standard conditions | 0.041 mm |
| Grease A, polishing test components, standard conditions | 0.033 mm |
| Grease A, polishing test components, break-in at 50 lbs. for 5 minutes | 0.018 mm |
| Grease A, polishing test components, break-in at 50 lbs. for 10 minutes | 0.032 mm |
| Grease A, break-in at 50 lbs. for 5 minutes | 0.028 mm |
| Grease A, break in at 50 lbs. for 10 minutes | 0.058 mm |

Additional Falex Pin and Vee Block Studies—Testing Effect of Flat Vee Blocks:

Again using fresh Grease A, various break-in and pre-treatment conditions for the falex pin and vee block were evaluated. The following conditions were employed:

Pre-polishing of test parts with TBS break-in fluid, 5 minutes at a 50-lb. load, followed by 15 minutes at 200 lbs., using standard vee blocks. Note, FIG. 41.

Pre-polishing of test parts with TBS break-in fluid, 5 minutes at a 50-lb. load followed by 15 minutes at 200 lbs., using flat vee blocks. Note, FIG. 42.

As observed before, breaking in at the 50-lb. load leads to a smoother torque profile, especially if a 5-minute break-in period is used. However, more wear and torque was observed with the flat vee blocks than the standard vee blocks. This may be of potential concern when using the flat vee blocks with grease.

More Wear Scar Measurements at 200 lbs.

| Grease A, Falex Pin and Vee Block Condition | Wear Scar |
|---|---|
| Break in at 50 lbs. for 5 minutes, 15 minutes at 200 lbs., Standard Vee Blocks | 0.005 mm |
| Break in at 50 lbs. for 5 minutes, 15 min at 200 lbs., Flat Vee Blocks | 0.053 mm |

Epilogue

The present new small scale grease wear testing method using a modified falex pin and vee block device including the present grease holder in an otherwise standard falex pin and vee block test machine, and absent its lubricant cup, provides an excellent means of evaluating the wear properties of greases. This new grease wear method has very good precision and an enhanced precision over that of ATSM D2266. The introduction of a thermocouple into the base of the pin allows for the collection of temperature during testing, information that could be very helpful to grease formulators in the development of new grease formulations and the assessment of different wear additives. The small sample size and short test duration time should also benefit grease formulators in their development of new grease products.

Thus, the present invention includes a completely new adaptation and modification of the falex pin and vee block device employed in standard ASTM D2760 testing, and a completely new method. In other words, now grease and other organic paste products can be tested according to modified ASTM D2760 equipment and methodology.

Also, failure analyses can be efficiently conducted in the practice of the instant invention.

Accordingly, the present invention is of inestimable value in testing and evaluation.

Computer and sensor equipment may be employed.

CONCLUSION TO THE INVENTION

The present invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous and sundry adaptations can be effected within its spirit, the literal claim scope of which is particularly pointed out by the following claims:

What is claimed is:

1. A method for evaluating wear resistance and its effects on a grease or another organic paste product, which comprises carrying out the following steps, which are not necessarily conducted in series:

(A) providing a revolving pin and test-load-transmitting vee block device having as the pin a cylindrical test journal; and having a pair of opposing vee blocks, each having a body with a pin-contacting surface that contacts the pin longitudinally when the opposing vee blocks are brought together with the pin held between them; said device including a grease holder that has the following:

a body in a form of a collar having an outer surface and an inner surface, and a first side and an opposing second side;

the first and second sides forming a hollow, open channel through the body defining the inner surface, and having a center axis, with the channel configured to receive the opposing vee blocks; and perpendicular to the center axis, a pair of opposing holes through the body, a first hole through the first side of the body and a second hole through the opposing second side of the body, with each hole defining a truncated cylindrical inside wall, which together provide pin-contacting surfaces and the through which the pin is inserted for contact with the pin-contacting surfaces of the inserted, opposing vee blocks, and for rotation during testing;

wherein said device is configured to receive and contain a sample of a grease or another organic past product such that the grease or the other organic paste product from the sample contacts the opposing pin-contacting surfaces of the inserted, opposing vee blocks, and the pin, during the testing, with containment of the sample provided through employment of the grease holder;

(B) assembling said device to include the grease holder, which includes inserting the opposing vee blocks into the hollow, open channel and inserting the pin so that it resides in the pair of opposing holes and comes into contact with the pin-contacting surfaces of the opposing vee blocks, and providing the sample of grease or other organic paste product thereto such that the sample is received and contained in said device;

(C) attaching said device with the sample to a rotating pin and test-load-transmitting vee block test machine; and (D) actuating the test machine with rotation of the pin and application of a test load to the pair of opposing vee blocks holding the pin while the pin rotates during the testing.

2. The method of claim 1, wherein the pin-contacting surfaces of the vee blocks are provided by V-shaped grooves, one V-shaped groove in each vee block, with the V-shaped grooves facing one another and receiving the pin.

3. The method of claim 2, wherein the test load is less than 400 lbs.; temperature of the pin and torque exerted in overcoming friction from contact of the pin-contacting surfaces of the vee blocks with the rotating pin are mead; and wear on the pin from maintaining the test load is calculated.

4. The method of claim 2, wherein the test load is no greater than about 250 lbs.; temperature of the pin and torque extended in overcoming friction from contact of the pin-contacting surfaces of the vee blocks with the rotating pin are measures; and wear on the pin from maintaining the test load is calculated.

5. The method of claim 4, wherein the sample is about 0.45-0.5 grams.

6. The method of claim 2, wherein the test load is implied stepwise for a predetermined time under at least two of the following loads; an about 50-lb. load, an about 100-lb. load, an about 150-lb. load, and an about 200-lb. load; temperature of the pin and torque exerted in overcoming friction from contact of the pin-contacting surfaces of the vee blocks with the rotating pin are measured; and wear on the pin from maintaining the test load is calculated.

7. The method of claim 6, wherein the sample is about 0.45-0.5 grams.

8. The method of claim 2, wherein the sample is about 0.45-0.5 grams.

9. The method of claim 1, wherein the test load is less than 400 lbs.; temperature of the pin and torque exerted in overcoming friction from contact of the pin-contacting surfaces of the vee blocks with the rotating pin are pleasured; and wear on the pin from maintaining the test load is calculated.

10. The method of claim 1, wherein the test load is no greater than about 250 lbs.; temperature of the pin and torque exerted in overcoming friction from contact of the pin-contacting surfaces of the vee blocks with the rotating pin are measured; and wear on the pin from maintaining the test load is calculated.

11. The method of claim 10, wherein the sample is about 0.45-0.5 grams.

12. The method of claim 1, wherein the test load is applied stepwise for a predetermined time under at least two of the following loads: an about 50-lb. load, an about 100-lb. load, an about 150-lb. load, and an about 200-lb. load; temperature of the pin and torque exerted in overcoming friction from contact of the pin-contacting surfaces of the vee blocks with the rotating pin are measured; and wear on the pin from maintaining the test load is calculated.

13. The method of claim 12, wherein the sample is about 0.45-0.5 grams.

14. The method of claim 1, wherein the sample is about 0.45-0.5 grams.

15. An article of manufacture comprising a grease wear test apparatus comprising a revolving pin and rest-load-transmitting vee block device having as the pin a cylindrical test journal; and having a pair of opposing vee blocks, each having a body with a pin-contacting surface that contacts the pin longitudinally when the opposing vee blocks are brought together with the pin held between them; said device further including a grease holder that has the following: A body in a form of a collar having an outer surface and an inner surface, and a first side and an opposing second side; the first and second sides forming a hollow, open channel through the body defining the inner surface, and having a center axis, with the channel configured to receive the opposing vee blocks; and perpendicular to the center axis, a pair of opposing holes through the body, a first hole through the first side of the body and a second hole through the opposing second side of the body, with each hole defining a truncated cylindrical inside wall, which together provide pin-contacting surfaces and the through which the pin is inserted for contact with the pin-contacting surfaces of the inserted, opposing vee blocks, and for rotation during testing; wherein said device is configured to receive and contain a sample of a grease or another organic past product such that the grease or the other organic paste product from the sample contacts the opposing pin-contacting surfaces of the inserted, opposing vee blocks, and the pin, during the testing, with containment of the sample provided through employment of the grease holder when the sample is present.

16. The article of claim 15, wherein the pin-contacting surfaces of the vee blocks are provided by V-shaped grooves, one V-shaped groove in each vee block, with the V-shaped grooves facing one another and configured for receiving the pin.

17. The article of claim 16, wherein the pin has a hole longitudinally along an axis of the pin about which the pin rotates during testing, which is configured to receive a thermocouple to measure temperature during the testing; and the thermocouple is present.

18. The article of claim 16, which is attached to a rotating pin and test-load-transmitting vee block test machine.

19. The article of claim 16, which is in kit form.

20. The article of claim 16, which is in assembled form.

21. The article of claim 15, wherein the pin has a hole longitudinally along an axis of the pin about which the pin rotates during testing, which is configured to receive a thermocouple to measure temperature during the testing; and the thermocouple is present.

22. The article of claim 15, which is attached to a rotating pin and test-load-transmitting vee block test machine.

23. The article of claim 15, which is in kit form.

24. The article of claim 15, which is in assembled form.

* * * * *